United States Patent

Hammond et al.

(10) Patent No.: US 6,417,217 B1
(45) Date of Patent: Jul. 9, 2002

(54) PROLINES AS ANTIMICROBIAL AGENTS

(75) Inventors: Milton L. Hammond, Somerville; Aaron H. Leeman, Cranford; Milana Maletic, Hoboken; Gina M. Santorelli, Oceanport; Sherman T. Waddell, Westfield, all of NJ (US); John Finn, Stow, MA (US); Michael Morytko, Framingham, MA (US); Siya Ram, Winchester, MA (US); Dennis Keith, Montclair, NJ (US)

(73) Assignees: Merck & Co., Inc., Rahway, NJ (US); Cubist Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/935,033

(22) Filed: Aug. 22, 2001

Related U.S. Application Data

(62) Division of application No. 09/566,112, filed on May 5, 2000, now Pat. No. 6,333,344.
(60) Provisional application No. 60/132,546, filed on May 5, 1999.

(51) Int. Cl.[7] .................. A61K 31/4184; A61K 31/422; A61K 31/427; A61K 31/437; A61K 31/52
(52) U.S. Cl. .................. 514/394; 514/266; 514/303; 514/365; 514/378
(58) Field of Search ................. 514/266, 303, 514/365, 378, 394

(56) References Cited

U.S. PATENT DOCUMENTS

| | | |
|---|---|---|
| 3,854,480 A | 12/1974 | Zaffaroni |
| 4,452,775 A | 6/1984 | Kent |
| 5,041,567 A | 8/1991 | Rogers et al. |
| 5,239,660 A | 8/1993 | Ooi |
| 5,705,487 A | 1/1998 | Schacht et al. |
| 5,726,195 A | 3/1998 | Hill et al. |

FOREIGN PATENT DOCUMENTS

| | | |
|---|---|---|
| WO | WO 95/05384 | 2/1995 |
| WO | WO 97/05132 | 2/1997 |

OTHER PUBLICATIONS

Richard M. Keenan, et al., *Bioorganic & Medicinal Chemistry Letters*, 8 pp 3165–3170 (1998).
James Gilbart, et al., *Antimicrobial Agents and Chemotherapy*, 37(1), pp 32–38 (1993).
Jacob J. Clement, et al., *Antimircrobial Agents and Chemotherapy*, 38 (5), pp 1071–1078 (1994).
Susumu Takada, et al., *J. Medicinal Chemistry*, 39, pp 2844–2851 (1996).
Daniel Kern, et al., *Biochemi*, 61, pp 1257–1272 (1979).

*Primary Examiner*—Laura L. Stockton
(74) *Attorney, Agent, or Firm*—James M. Hunter, Jr.; Mark R. Daniel

(57) ABSTRACT

Transfer ribonucleic acid (tRNA) synthetase inhibitors, salts, and pharmaceutically acceptable compositions thereof of the general formula:

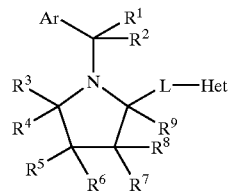

wherein Ar is aryl and heteroaryl; L is —C(O)N(Q)CH$_2$—, or —CR$^{10}$R$^{11}$OCR$^{12}$R$^{13}$—; Q is hydrido, —(CH$_2$)$_m$CO$_2$H and —(CH$_2$)$_m$CO$_2$CH$_3$, m is 1, 2, 3, and 4; R$^1$, R$^2$, R$^9$, R$^{10}$, R$^{11}$, R$^{12}$ and R$^{13}$ are hydrido or lower alkyl; wherein Het is a heterocyclic moiety, the inhibitors are suitable for use as antimicrobial agents.

13 Claims, No Drawings

PROLINES AS ANTIMICROBIAL AGENTS

This is a division of application Ser. No. 09/566,112 filed May 5, 2000 now U.S. Pat. No. 6,333,344, which claims benefit of Provision application Ser. No. 60/132,546, filed May 5, 1999.

FIELD OF THE INVENTION

This invention relates to the field of transfer ribonucleic acid (tRNA) synthetase inhibitors, their preparation and their use as antimicrobial agents.

BACKGROUND OF THE INVENTION

Aminoacyl tRNA synthetases (aaRS) are a family of essential enzymes that are found in virtually every biological cell and are responsible for maintaining the fidelity of protein synthesis. They specifically catalyze the aminoacylation of tRNA in a two step reaction:

amino acid (AA)+ATP=>AA-AMP+PPi

AA-AMP+tRNA=>tRNA-AA+AMP

The enzyme binds adenosine triphosphate (ATP) and its specific amino acid to catalyze formation of an aminoacyl adenylate complex (AA-AMP) with concomitant release of pyrophosphate (PPi). In the second step, the amino acid is transferred to the 2' or 3' terminus of the tRNA yielding "charged" tRNA and adenosine monophosphate (AMP). The charged tRNA delivers the amino acid to the nascent polypeptide chain on the ribosome.

There are at least twenty essential enzymes in this family for each organism. Inhibition of any of the essential tRNA synthetases disrupts protein translation, ultimately resulting in growth inhibition. Pseudomonic acid A, an antibacterial agent currently used in human therapy, provides clear evidence of the utility of tRNA synthetase inhibitors as useful pharmaceuticals. Pseudomonic acid A binds to one particular tRNA synthetase, isoleucyl tRNA synthetase, and inhibits isoleucyl adenylate formation in several Gram positive bacterial pathogens such as *Staphylococcus aureus*, resulting in the inhibition of protein synthesis, followed by growth inhibition. Novel synthetic compounds that target tRNA synthetases offer clear advantages as useful therapeutic agents to curb the threat of drug resistance. Drug resistance allows a pathogen to circumvent the biochemical disruption caused by an antimicrobial agent. This resistance can be a result of a mutation that has been selected for and maintained. Pathogens in the environment have had repeated exposure to current therapeutics. This exposure has led to the selection of variant antimicrobial strains resistant to these drugs.

Novel synthetic antimicrobial agents, therefore, would be expected to be useful to treat drug resistant pathogens, since the pathogen has never been exposed to the novel antimicrobial agent. The development of compounds or combinations of compounds targeting more than one tRNA synthetase is also advantageous. Accordingly, inhibition of more than one enzyme should reduce the incidence of resistance since multiple mutations in a pathogen would be required and are statistically rare.

SUMMARY OF THE INVENTION

The present invention discloses novel compounds which inhibit tRNA synthetases and have efficacy, including whole cell killing, against a broad spectrum of bacteria and fungi. Described herein are compounds that exhibit tRNA synthetase inhibition.

The present invention comprises, in one aspect, compounds of Formula I.

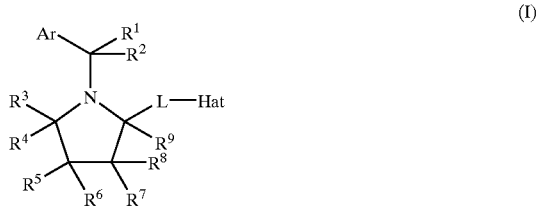

(I)

Group Ar of Formula I is selected from aryl or heteroaryl. Preferably, Ar is aryl, more preferably, substituted phenyl, even more preferably, 2,4-dichlorophenyl.

Group L of Formula I is selected from —C(O)N(Q)CH$_2$—, or —CR$^{10}$OR$^{11}$OCR$^{12}$R$^{13}$—; wherein Q is selected from hydrido, —(CH$_2$)$_m$CO$_2$H or —(CH$_2$)$_m$CO$_2$CH$_3$; and wherein m is a whole number from 1–4. Preferably, L is —C(O)NHCH$_2$—.

Each of substituents R$^1$, R$^2$, R$^9$, R$^{10}$, R$^{11}$, R$^{12}$, and R$^{13}$ of Formula I is independently selected from hydrido or lower alkyl, preferably hydrido.

Each of substituents R$^3$, R$^4$, R$^5$, R$^6$, R$^7$, and R$^8$ of Formula I is independently selected from hydrido, acyl, amino, cyano, acyloxy, acylamino, carboalkoxy, carboxyamido, carboxy, halo, thio, alkyl, heteroaryl, heterocyclyl, alkoxy, aryloxy, sulfoxy, N-sulfonylcarboxyamido, N-acylamino sulfonyl, hydroxy, aryl, cycloalkyl, sulfinyl, or sulfonyl. Additionally, R$^3$ and R$^4$ together or R$^5$ and R$^6$ together or R$^7$ and R$^8$ together are selected from

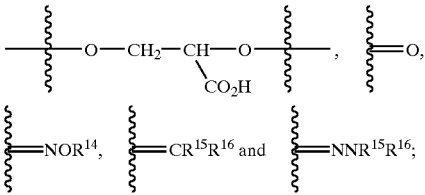

wherein each of R$^{14}$, R$^{15}$ and R$^{16}$ is independently selected from hydrido, alkyl or carboxy-substituted alkyl; provided that at least five of R$^3$, R$^4$, R$^5$, R$^6$, R$^7$, and R$^8$ are independently hydrido. Preferably, each of R$^3$, R$^4$, R$^5$, R$^6$, R$^7$, and R$^8$ is independently selected from hydrido, hydroxy, alkoxy, alkyl, amino, and carboxyamido. More preferably, each of R$^3$, R$^4$, R$^5$, R$^6$, R$^7$, and R$^8$ is independently selected from hydrido, —O(CH$_2$)$_n$CO$_2$R$^{17}$, —O(CH$_2$)$_n$CONHSO$_2$R$^{18}$, —(CH$_2$)$_n$CO$_2$R$^{19}$, —(CH$_2$)$_n$CONHSO$_2$R$^{20}$, —C(O)NHCH(R$^{22}$)CO$_2$R$^{21}$, or —N(R$^{23}$)(CH$_2$)$_n$CO$_2$R$^{24}$, wherein each of R$^{17}$, R$^{19}$, R$^{21}$, R$^{22}$, R$^{23}$, and R$^{24}$ is independently selected from hydrido or alkyl; wherein each of R$^{18}$ and R$^{20}$ is independently alkyl; wherein n is selected from 1 or 2. Even more preferably, each of R$^3$, R$^4$, R$^6$, R$^7$, and R$^8$ is hydrido and R$^5$ is selected from —O(CH$_2$)$_n$CO$_2$R$^{17}$, —O(CH$_2$)$_n$CONHSO$_2$R$^{18}$, —(CH$_2$)$_n$CO$_2$R$^{18}$, —(CH$_2$)$_n$CONHSO$_2$R$^{20}$, C(O)NHCH(R$^{22}$)—CO$_2$R$^{21}$, or —N(R$^{23}$)$_n$(CH$_2$)$_n$CO$_2$R$^{24}$.

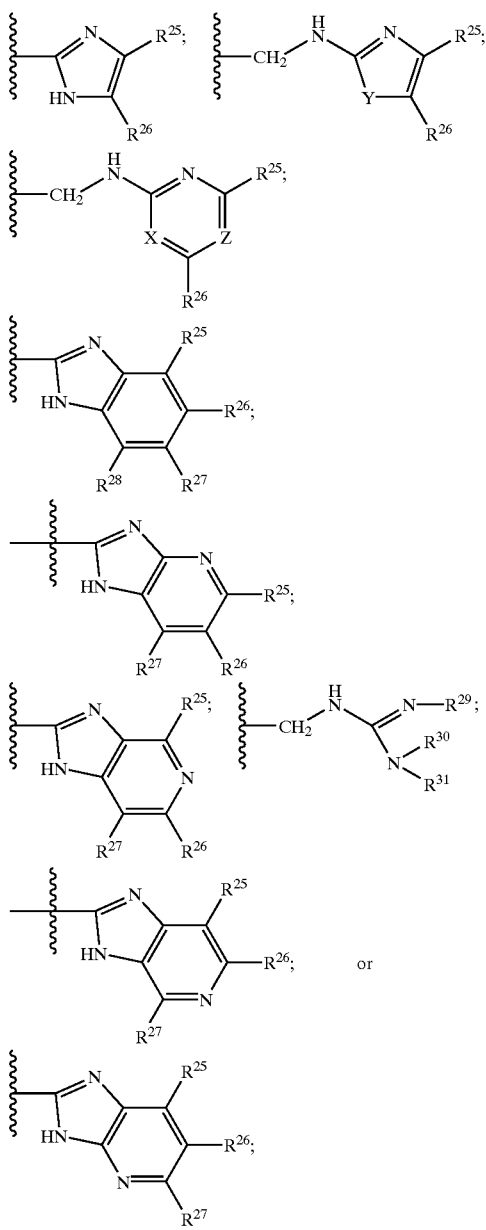

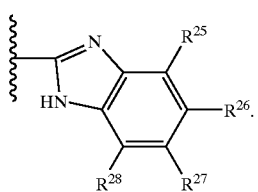

wherein X is selected from N or $CR^{27}$; wherein Y is selected from NH, S or O, wherein Z is selected from N or $CR^{28}$; wherein each of $R^{25}$, $R^{26}$, $R^{27}$, and $R^{28}$ is independently selected from nitro, halo, hydroxy, lower amino, lower alkyl, lower alkoxy, aryloxy, lower carboalkoxy, sulfinyl, sulfonyl, carboxy, lower thio, and sulfoxy; and wherein each of $R^{29}$, $R^{30}$, and $R^{31}$ is selected from hydrido, alkyl, aryl, nitro, amino, sulfonyl or sulfinyl. Preferably, Hat is The invention also embraces pharmaceutically-acceptable salts of the forgoing compounds.

A further aspect of the invention comprises using a composition comprising the compound(s) of Formula I to inhibit a tRNA synthetase and in particular, to modulate the growth of bacterial or fungal organisms in mammals, a plant or a cell culture.

Yet another aspect of the invention involves a method of inhibiting the growth of microorganisms. The method involves exposing the microorganism to a compound of the invention, preferably a compound of Formula I, under conditions whereby a therapeutically effective amount of the compound enters the microorganism. The method is useful for inhibiting the growth of microrganisms in vivo and in vitro.

Another aspect of the invention is a pharmaceutical composition comprising the compound(s) of the invention and, in particular, the compounds of Formula I, useful in the treatment of microbial infections, e.g., bacterial infections, fungal infections. A related aspect of the invention is a method of making a medicament which involves placing a compound(s) of the invention, preferably a compound of Formula I, in a suitable pharmaceutically acceptable carrier.

These and other aspects of the invention will be more apparent in reference to the following detailed description of the invention.

DETAILED DESCRIPTION OF THE INVENTION

I. Definitions

Molecular terms, when used in this application, have their common meaning unless otherwise specified. The term "hydrido" denotes a single hydrogen atom (H). The term "acyl" is defined as a carbonyl radical attached to a hydrido, alkyl, alkenyl, alkynyl, cycloalkyl, heterocycyl, aryl or heteroaryl group, examples of such radicals being formyl, acetyl and benzoyl. The term "amino" denotes a nitrogen radical containing two substituents independently selected from the group consisting of hydrido, alkyl, cycloalkyl, heterocyclyl, aryl, and heteroaryl. Preferred amino radicals are $NH_2$ radicals and "lower amino" radicals, whereby the two substituents are independently selected from hydrido and lower alkyl. A subset of amino is "alkylamino", whereby the nitrogen radical contains at least 1 alkyl substituent. Preferred alkylamino groups contain alkyl groups that are substituted, for example, with a carboalkoxy group. The term "acyloxy" denotes an oxygen radical adjacent to an acyl group. The term "acylamino" denotes a nitrogen radical adjacent to an acyl, carboalkoxy or carboxyamido group. The term "carboalkoxy" is defined as a carbonyl radical adjacent to an alkoxy or aryloxy group. The term "carboxyamido" denotes a carbonyl radical adjacent to an amino group. A subset of carboxyamido is "N-sulfonylcarboxyamido" which denotes a carbonyl radical adjacent to an N-sulfonyl-5 substituted amino group. The term "halo" is defined as a bromo, chloro, fluoro or iodo radical. The term "thio" denotes a sulfur radical adjacent to a substituent group selected from hydrido, alkyl, cycloalkyl, heterocyclyl, aryl and heteroaryl, such as, methylthio and phenylthio. Preferred thio radicals are "lower thio" radicals containing lower alkyl groups.

The term "alkyl" is defined as a linear or branched, saturated radical having one to about ten carbon atoms unless otherwise specified. Preferred alkyl radicals are "lower alkyl" radicals having one to about five carbon atoms. One or more hydrogen atoms can also be replaced by a substitutent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Preferred substituents are carboalkoxy, carboxy, N-sulfonylcarboxyamido, and N-acylaminosulfonyl. Examples of alkyl groups include methyl, tert-butyl, isopropyl, methoxymethyl, carboxymethyl, and carbomethoxymethyl. The term "alkenyl" embraces linear or branched radicals having two to about twenty carbon atoms, preferably three to about ten carbon atoms, and containing at least one carbon-carbon double bond. One or more hydrogen atoms can also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Examples of alkenyl groups include ethylenyl or phenyl ethylenyl. The term "alkynyl" denotes linear or branched radicals having from two to about ten carbon atoms, and containing at least one carbon-carbon triple bond. One or more hydrogen atoms can also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Examples of alkynyl groups include propynyl. The term "aryl" denotes aromatic radicals in a single or fused carbocyclic ring system, having from five to twelve ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Examples of aryl groups include phenyl, 2,4-dichlorophenyl, naphthyl, biphenyl, terphenyl. "Heteroaryl" embraces aromatic radicals that contain one to four hetero atoms selected from oxygen, nitrogen and sulfur in a single or fused heterocyclic ring system, having from five to fifteen ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Examples of heteroaryl groups include, tetrazolyl, pyridinyl, thiazolyl, thiadiazoyl, isoquinolinyl, pyrazolyl, oxazolyl, oxadiazoyl, triazolyl, and pyrrolyl groups.

The term "cycloalkyl" is defined as a saturated or partially unsaturated carbocyclic ring in a single or fused carbocyclic ring system having from three to twelve ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Examples of a cycloalkyl group include cyclopropyl, cyclobutyl, cyclohexyl, and cycloheptyl. The term "heterocyclyl" embraces a saturated or partially unsaturated ring containing zero to four hetero atoms selected from oxygen, nitrogen and sulfur in a single or fused heterocyclic ring system having from three to twelve ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, sulfinyl, sulfonyl, N-sulfonylcarboxyamido, and N-acylaminosulfonyl. Examples of a heterocyclyl group include morpholinyl, piperidinyl, and pyrrolidinyl. The term "alkoxy" denotes oxy-containing radicals substituted with an alkyl, cycloalkyl or heterocyclyl group. Examples include methoxy, tert-butoxy, benzyloxy and cyclohexyloxy. Preferred alkoxy radicals are "lower alkoxy" radicals having a lower alkyl substituent. The term "aryloxy" denotes oxy-containing radicals substituted with an aryl or heteroaryl group. Examples include phenoxy. The term "sulfinyl" is defined as a tetravalent sulfur radical substituted with an oxo substituent and a second substituent selected from the group consisting of alkyl, cycloalkyl, heterocyclyl, aryl and heteroaryl. The term "sulfonyl" is defined as a hexavalent sulfur radical substituted with two oxo substituents and a third substituent selected from alkyl, cycloalkyl, heterocyclyl, aryl and heteroaryl. The term "N-acylaminosulfonyl" denotes a hexavalent sulfur atom bound to two oxo substituents and an N-acyl-substituted amino group.

The pharmaceutically-acceptable salts of the compounds of the invention (preferably a compound of Formula I) include acid addition salts and base addition salts. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compounds of the invention (preferably a compound of Formula I) may be prepared from an inorganic acid or an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts of compounds of the invention (preferably a compound of Formula I) include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine and procaine. All of these salts may be prepared by conventional means from the corresponding compound of the invention (preferably a compound of Formula I) by treating, for example, the compound of the invention (preferably a compound of Formula I) with the appropriate acid or base.

As used herein, "treating" means preventing the onset of, slowing the progression of, or eradicating the existence of the condition being treated, such as a microbial infection. Successful treatment is manifested by a reduction and, preferably, an eradication of the bacterial and/or fungal infection in the subject being treated.

The compounds of the invention (preferably compounds of Formula I) can possess one or more asymmetric carbon atoms and are thus capable of existing in the form of optical isomers as well as in the form of racemic or non-racemic mixtures thereof. The compounds of the invention (preferably compounds of Formula 1) can be utilized in the present invention as a single isomer or as a mixture of stereochemical isomeric forms. Diastereoisomers can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of the invention (preferably compounds of Formula I) with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention (preferably compounds of Formula I) can likewise be obtained by utilizing optically active starting materials. These isomers may be in the form of a free acid, a free base, an ester or a salt.

The invention also embraces isolated compounds. An isolated compound refers to a compound which represents at least 10%, preferably 20%, more preferably 50% and most preferably 80% of the compound present in the mixture, and exhibits a detectable (i.e. statistically significant) antimicrobial activity when tested in conventional biological assays such as those described herein.

II. Description

According to one aspect of the invention, compounds of Formula I are provided. The compounds are useful for inhibiting the enzymatic activity of a tRNA synthetase in vivo or in vitro. The compounds are particularly useful as antimicrobial agents, i. e., agents that inhibit the growth of bacteria or fungi.

One sub-class of compounds of Formula I are compounds of Formula II (II)

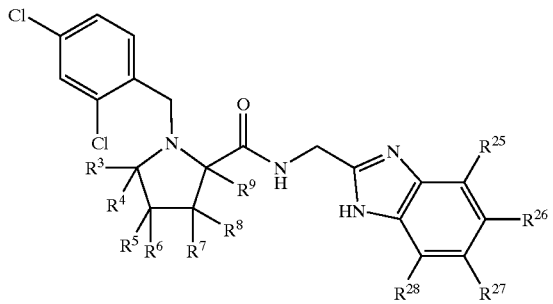

Substituents $R^3$, $R^4$, $R^5$, $R^6$, $R^7$, $R^8$, $R^9$, $R^{25}$, $R^{26}$, $R^{27}$ and $R^{28}$ are as previously described.

The compounds of the invention (preferably compounds of Formula I) are active against a variety of bacterial organisms. They are active against both Gram positive and Gram negative aerobic and anaerobic bacteria, including Staphylococci, for example *S. aureus;* Enterococci, for example *E. faecalis;* Streptococci, for example *S. pneumo-*

*niae;* Haemophilus, for example *H. influenza;* Moraxella, for example *M. catarrhalis;* and Escherichia, for example *E. coli.* The compounds of the present invention (preferably compounds of Formula I) are also active against Mycobacteria, for example *M. tuberculosis.* The compounds of the present invention (preferably compounds of Formula I are also active against intercellular microbes, for example Chlamydia and Rickettsiae. The compounds of the present invention (preferably compounds of Formula I) are also active against Mycoplasma, for example *M. pneumoniae.*

The compounds of the present invention (preferably compounds of Formula I) are also active against fungal organisms, including, among other organisms, the species Aspergillus, Blastomyces, Candida, Coccidioides, Cryptococcus, Epidermophyton, Hendersonula, Histoplasma, Microsporum, Paecilomyces, Paracoccidioides, Pneumocystis, Trichophyton, and Trichosporium.

In a second aspect the invention provides a pharmaceutical composition comprising a compound of the invention, preferably a compound in accordance with the first aspect of the invention, and a pharmaceutically-acceptable carrier (described below). As used herein the phrase "therapeutically-effective amount" means that amount of a compound of the present invention (preferably a compound of Formula I) which prevents the onset of, alleviates the symptoms of, or stops the progression of a microbial infection. The term "microbial" means bacterial and fungal, for example a "microbial infection" means a bacterial or fungal infection. The term "treating" is defined as administering, to a subject, a therapeutically-effective amount of a compound of the invention (preferably a compound of Formula I). The term "subject", as described herein, is defined as a mammal, a plant or a cell culture.

According to another aspect of the invention, a method for inhibiting a tRNA synthetase is provided which comprises contacting a tRNA synthetase with a compound of the invention (preferably a compound of Formula I) under the conditions whereby the tRNA synthetase interacts with its substrates and its substrates react(s) to form an aminoacyl adenylate intermediate and, preferably, react(s) further to form a charged tRNA. Such conditions are known to those skilled in the art (see also e. g., the Examples for conditions), and PCT/US 96/11910, filed Jul. 8, 1996 (WO 97/05132, published Feb. 3, 1997), and U.S. Pat. No. 5,726,195. This method involves contacting a tRNA synthetase with an amount of compound of the invention (preferably a compound of Formula I) that is sufficient to result in detectable tRNA synthetase inhibition. This method can be performed on a tRNA synthetase that is contained within an organism or outside an organism.

In a further aspect, the invention provides a method for inhibiting the growth of microorganisms, preferably bacteria or fungi, comprising contacting said organisms with a compound of the invention (preferably a compound of Formula I) under conditions which permit entry of the compound into said organism and into said microorganism. Such conditions are known to one skilled in the art and are exemplified in the Examples. This method involves contacting a microbial cell with a therapeutically-effective amount of compound(s) of the invention (preferably compound(s) of Formula I), e.g. to inhibit cellular tRNA synthetase in vivo or in vitro. This method is used in vivo, for example, for treating microbial infections in mammals. Alternatively, the method is used in vitro, for example, to eliminate microbial contaminants in a cell culture, or in a plant.

In accordance with another aspect of the invention, the compositions disclosed herein are used for treating a subject afflicted by or susceptible to a microbial infection. The method involves administering to the subject a therapeutically effective amount of a compound of the invention (preferably a compound of Formula I). According to this aspect of the invention, the novel compositions disclosed herein are placed in a pharmaceutically acceptable carrier and are delivered to a recipient subject (preferably a human) in accordance with known methods of drug delivery. Exemplary procedures for delivering an antibacterial, antifungal and antimycoplasmal agent are described in U.S. Pat. No. 5,041,567, issued to Rogers and in PCT patent application number EP94/02552 (publication no. WO 95/05384), the entire contents of which documents are incorporated in their entirety herein by reference. In general, the methods of the invention for delivering the compositions of the invention in vivo utilize art-recognized protocols for delivering the agent with the only substantial procedural modification being the substitution of the compounds of the invention (preferably compounds of Formula I) for the drugs in the art-recognized protocols. Likewise, the methods for using the claimed composition for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the invention (preferably compounds of Formula I) for the agents used in the art-recognized protocols.

The pharmaceutical preparations disclosed herein are prepared in accordance with standard procedures and are administered at dosages that are selected to reduce, prevent or eliminate the infection (See, e. g., Remington's Pharmaceutical Sciences, Mack Publishing Company, Easton, Pa. and Goodman and Gilman's The Pharmaceutical Basis of Therapeutics, Pergamon Press, New York, N.Y., the contents of which are incorporated herein by reference, for a general description of the methods for administering various antimicrobial agents for human therapy). The compositions of the invention (preferably of Formula I) can be delivered using controlled (e.g., capsules) or sustained release delivery systems (e.g., bioerodable matrices). Exemplary delayed release delivery systems for drug delivery that are suitable for administration of the compositions of the invention (preferably of Formula I) are described in U.S. Pat. Nos. 4,452,775 (issued to Kent), U.S. Pat. No. 5,239,660 issued to Leonard), U.S. Pat. No. 3,854,480 (issued to Zaffaroni).

The pharmaceutically-acceptable compositions of the present invention comprise one or more compounds of the invention (preferably compounds of Formula I) in association with one or more nontoxic, pharmaceutically-acceptable carriers and/or diluents and/or adjuvants and/or excipients, collectively referred to herein as "carrier" materials, and if desired other active ingredients.

The compounds of the present invention (preferably compounds of Formula I) are administered by any route, preferably in the form of a pharmaceutical composition adapted to such a route, as illustrated below and are dependent on the condition being treated. The compounds and compositions can be, for example, administered orally, intravascularly, intraperitoneally, subcutaneously, intramuscularly or topically.

For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

The pharmaceutical compositions can be administered via injection. Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compounds of the present invention can be in powder form for reconstitution in the appropriate pharmaceutically acceptable carrier at the time of delivery.

The dosage regimen for treating an infection with the compound and/or compositions of this invention is selected in accordance with a variety of factors, including the type, age, weight, sex and medical condition of the patient, the severity of the infection, the route and frequency of administration and the particular compound employed. In general, dosages are determined in accordance with standard practice for optimizing the correct dosage for treating an infection.

The compositions can contain from 0.1% to 99% by weight, preferably 10–60% by weight, of the active ingredient, depending on the method of administration. If the compositions contain dosage units, each dosage unit preferably contains from 50–500 mg of the active material. For adult human treatment, the dosage employed preferably ranges from 100 mg to 3 g, per day, depending on the route and frequency of administration.

If administered as part of a total dietary intake, the amount of compound employed can be less than 1% by weight of the diet and preferably no more than 0.5% by weight. The diet for animals can be normal foodstuffs to which the compound can be added or it can be added to a premix.

Further references to features and aspects of the invention are provided in the Examples set out hereafter.

EXAMPLES

The following Examples are detailed descriptions of the methods of preparation of compounds of Formula I. These detailed preparations fall within the scope of, and serve to exemplify, the invention. These Examples are presented for illustrative purposes only and are not intended as a limitation on the scope of the invention.

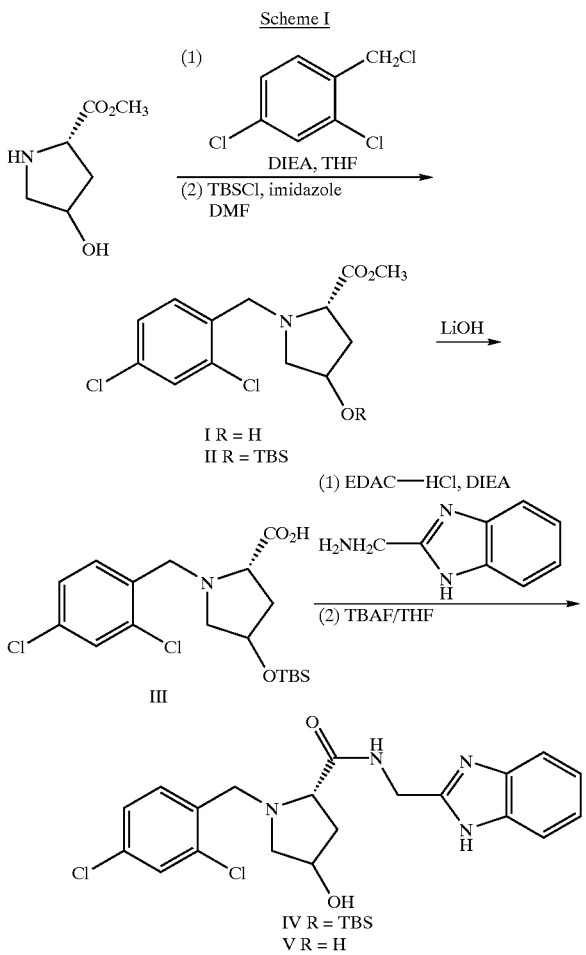

Synthesis of I

To 10.0 g of 4-hydroxy-L-proline methylester in 100 ml of anhydrous tethydrofuran was added 10.5 ml of 2,4-dichlorobenzylchloride, 30 ml of diisopropylethylamine, and 100 mg of tetrabutylammonium iodide, respectively. The reaction was allowed to stir for 16 hours at room temperature before partitioning with 200 ml ethyl acetate and 300 ml 1 N hydrochloric acid. The acid layer was neutralized with sodium hydrogen carbonate and extracted with 300 ml ethyl acetate. The organic layer was dried with 10 g sodium sulfate and poured through 100 g of silica gel. The solution was concentrated to yield 16.8 g of I as a clear oil.

Synthesis II

To 16.8 g of I in 50 ml anhydrous N,N'-dimethylformamide was added 9.2 g of tert-butyldimethylsilyl chloride followed by 4.5 g imidazole. The reaction was allowed to stir at room temperature for 16 hours before partitioning with 300 ml ethylacetate and (2×400 ml) brine. The organic layer was dried with 10 g sodium sulfate and poured through 100 g of silica gel. The solution was concentrated to afford 23 g of II as a yellow oil.

Synthesis III

At 0° C., 23.0 g of II in 50 ml methanol and 50 ml 1,4-dioxane was added to a solution of 2.5 g lithiumhydroxide monohydrate in 25 ml water. After 1 hour, the reaction mixture was partitioned with 250 ml ethyl acetate and 250 ml dilute citric acid. The organic layer was washed with 200 ml brine then dried with 10 g sodium sulfate. Concentration in vacu yielded 19.1 g of II as a yellow oil.

Synthesis IV

To 0.36 g III in 10 ml anhydrous N,N'-dimethylformamide was added 0.26 g 2-(aminomethyl) benzimidazole dihydrochloride, 1.1 ml diisopropylethylamine and 0.22 g 1-(3-dimethylaminoproply)-3-ethylcarbodiimide hydrochloride, respectively. The reaction was stirred for 16 hours at room temperature before partitioning with 30 ml ethylacetate and 2×50 ml brine. The organic layer was dried with 0.5 g sodium sulfate then concentrated to dryness. Purification by silica gel chromatography gave 0.20 g of IV.

Synthesis V

A solution of 0.20 g IV in 4 ml of 1 M tetrabutylammonium fluoride in tetrahydrofuran was stirred at room temperature for 16 hours. The reaction was concentrated and purified by silica gel chromatography using 10% methanol in dichloromethane to give 0.07 g of V as a white solid.

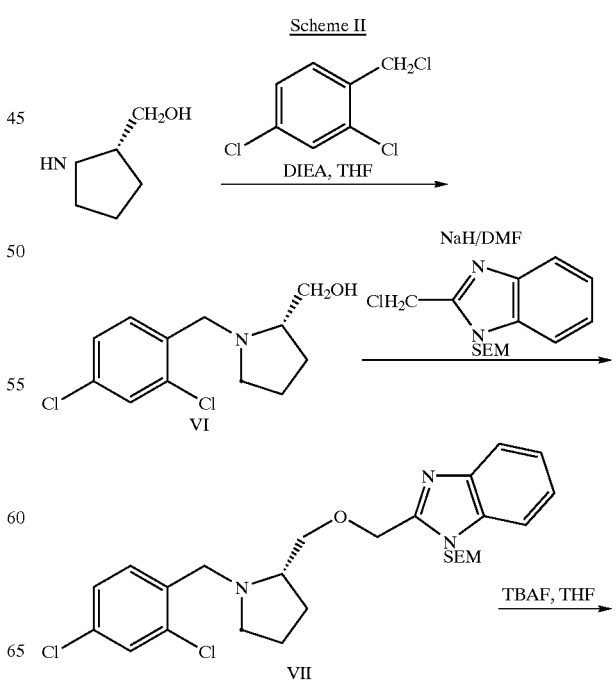

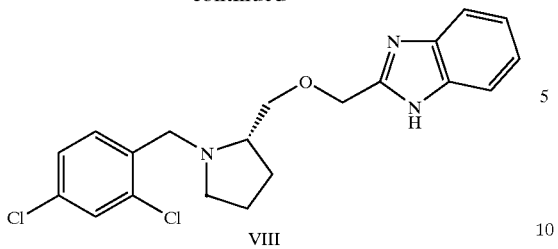

VIII

Synthesis of VI

A solution of 5.0 g of S-pyrrolidine methanol, 7.6 ml of 2,4-dichlorobenzyl chloride, 17.3 ml diisopropylethylamine and 0.1 g tetrabutylammoniam iodide in 100 ml anhydrous tetrahydrofuran was stirred at room temperature for 18 hours before partitioning with 200 ml ethylacetate and 200 ml 1N hydrochloric acid. The acid layer was neutralized with sodium bicarbonate then extracted with 200 ml ethyl acetate. The organic layer was washed with 200 ml brine and dried with 10 g sodium sulfate. Concentration of the organic solution gave 10.3 g of VI as an oil.

Synthesis of VII 0.43 g of VI was added to 0.07g of 60% NaH in 10 ml anhydrous N,N'-Dimethylformamide. After stirring at room temperature for 1 hour, the chlormethylbenzimidazole II was added. The reaction was stirred for 18 hours before partitioning with 50 ml ethyl acetate and 50 ml brine. The organic layer was dried with 5 g sodium sulfate and concentrated. The crude oil was purified by silica gel chromatography using 1:1 hexane/ethyl acetate to give 0.56 g of VII.

Synthesis of VIII

To 0.56 g of VII in 5 ml 1,4-dioxane was added 0.2 ml concentrated hydrochloric acid. The reaction was heated at 100° C. for 2 hours before partitioning with 30 ml ethyl acetate and 30 ml saturated solution of sodium bicarbonate. The organic layer was washed with 30 ml brine and dried with 2 g sodium sulfate. Concentration of the organic layer afforded 0.4 g of VIII as an oil.

Scheme III

Synthesis IX
Modular Synthesis Of 3- And 4-Hydroxyproline Analogues

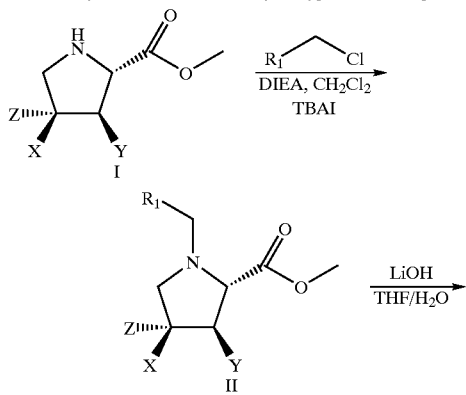

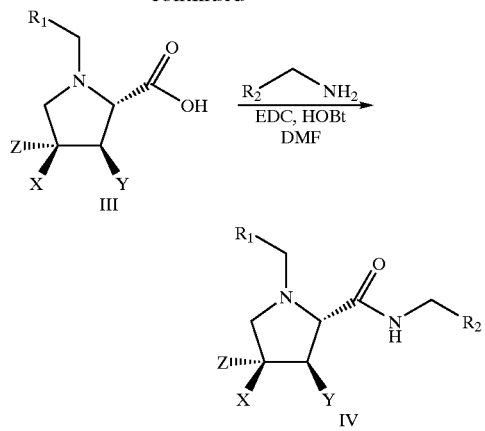

Synthesis of N-alkylated Hydroxy Proline Methyl Esters (II)

To a suspension of hydroxy-L-Proline methyl ester hydrochloride (I,1.1 mmol, 200 mg) in 3 ml dichloromethane in a 16 mm tube with a screw cap lid was added diisopropylethylamine (DIEA, 2.43 mmol, 0.43 ml). The suspension was sonicated for 2 minutes, then aryl chloride ($R_1CH_2Cl$, 1.05 mmol) and tetrabutylammonium iodide (TBAI, 0.05 mmol, 20 mg) were added. Reaction mixture was heated at 40° C. for 24 hr then cooled to room temperature and diluted with 5 ml of dichloromethane and 5 ml of aqueous saturated sodium bicarbonate. The reaction mixture was shaken vigorously and the layers were separated. The organic layer was collected in a clean 16 mm tube and the solvent was evaporated under nitrogen stream to yield crude N-alkylated hydroxy proline II. Each intermediate was characterized by LC/MS and yielded a major peak corresponding to the molecular ion.

Trans-3-hydroxy-L-proline methyl ester hydrochloride (I, X=Z=H, Y=OH) was prepared by dissolving the corresponding trans-3-hydroxy-L -proline (7.6 mmol, 1 g) in 20 ml of methanol and 15 ml of 1M hydrochloric acid in ether. The reaction mixture was refluxed for 3 hr, then cooled the room temperature and stripped in vacuo to yield a white solid (1.2 g).

Aryl chlorides used for these displacements were obtained from commercial sources: 2-chlorobenzyl chloride (0.14 ml), 2,6-dichlorobenzyl chloride (215 mg), 6-chloropiperonyl chloride (225 mg), 2-chloro-4-nitrobenzyl chloride (226 mg), 3,4-dichlorobenzyl chloride (0.15 ml), 2,3-dichlorobenzyl chloride (0.15 ml), 2,5-dichlorobenzyl chloride (0.15 ml), 2,4-dichlorobenzyl chloride (0.15 ml), and 2-(4-chlorophenyl)-4-chloromethyl thiazole (265 mg).

Hydrolysis of Methyl Esters to Acids (III)

To a glass tube containing a suspension of 11 (1.05 mmol) in 6 ml of 1:1 mixture of THF and water was added lithium hydroxyde monohydrate (2.2 mmol, 53 mg). The reaction mixture was stirred at room temperature for 2 hrs to yield a clear, colorless solution that was then diluted with 10 ml of saturated aqueous sodium bicarbonate. The aqueous layer was washed three times with 5 ml of dichloromethane and the organic phase was discarded. The aqueous phase was then acidified to pH 1 with 6N hydrochloric acid, frozen and lyophilized overnight. The acid (III) was analyzed by LC/MS and yielded pure material corresponding to the molecular ion.

Acid intermediate in the synthesis of amide compound 8 (Table 1a): $\delta_H$ (DMSO-d6) 1.65 (1H, m), 2.05 (2H, m), 3.10 (2H, m), 3.30 (1H, m), 3.55 (1H, d, J=15 Hz), 4.10 (1H, d, J=15 Hz), 7.36(1H, dd, J$_1$=2.0 Hz, J$_2$=8.5 Hz), 7.49 (1H, d, J=2.0 Hz), 7.62 (1H, d, 8.5 Hz).

Amide Formation (IV)

Acid (III, 0.18 mmol) was dissolved in 0.8 ml of anhydrous acetonitrile and 0.2 ml of DIEA. To this slightly cloudy solution were added amine (0.18 mmol), hydroxybenzotriazole hydrate (0.18 mmol) and finally 1-ethyl-3-(3-dimethylaminopropyl)carbodiimide (EDC). The reaction mixtures were stirred at room temperature for 16 hours, then diluted with 2 ml of ethyl acetate. The organic layer was washed with 3 ml of saturated aqueous sodium bicarbonate and collected into a 16 mm test tube. The solvent was evaporated under a nitrogen stream and solid material was redissolved in 2 ml of 1:1 water/acetonitrile mixture. Sample was purified by HPLC using YMC-Pack ODS (100×20 mm) column; eluting with a gradient of 90% 0.1% TFA/water to 100% 0.1% TFA in acetonitrile over 10 min. at 20 ml/min, detecting at 254 nm. The largest peak was collected and analyzed by LC/MS (ESI) to yield a single UV peak corresponding to the molecular ion. Pure fully elaborated product was obtained as a bis-TFA salt by freezing and lyophilizing the fraction containing the largest peak.

Compound 8, (Table 1a): $\delta_H$ (CD$_3$OD) 2.23 (1H, m), 2.58 (1H, m), 3.36 (1H, m), 3.76 (1H, dd, J$_1$=4.5 Hz, J$_2$=12.5 Hz), 4.58 (2H, m), 4.63 (1H, m), 4.70 (1H, d, J=13.2 Hz), 4.78 (1H, d, J=16.4 Hz), 4.88 (1H, d, J=16.4 Hz), 7.32 (1H, dd, J$_1$=2.0 Hz, J$_2$=8.4 Hz), 7.48 (1H, d, J=2.0), 7.58 (3H, m), 7.78 (2H, m).

Amines used in this sequence were: 2-(aminomethyl) benzimidazole dihydrochloride, 2-(aminomethyl)-4,5-dimethylbenzimidazole, 2-(aminomethyl)-4-carboxymethylbenzimidazole, 2-(aminomethyl)-4-chlorobenzimidazole, 2-(aminomethyl)-4,5-dichlorobenzimidazole, 2-(aminomethyl)-4-aminobenzimidazole. These benzimidazole analogs were prepared according to the procedure described by Keenan, R. M. et al. (*Bioorg. Med. Chem Lett.* 1998, 8, 3165–3170).

Herein below, Tables 1a and 1b provide 4-hydroxyproline derivatives with unsubstituted and substituted benzimidazoles, respectively; Table 2a provides 3-hydroxyproline analogs with unsubstituted benzimidazoles; and Table 2b provides 3-hydroxyproline analogs with substituted benzimidazoles.

TABLE 1a 4-hydroxyproline derivatives containing unsubstituted benzimidazole

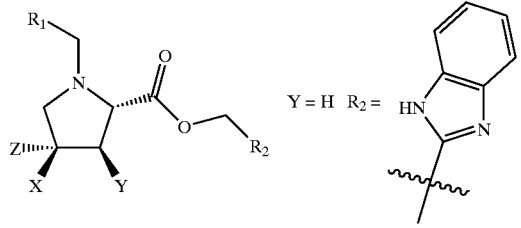

| Cmpd. | X | Z | R1 | Structure | MS Data |
|---|---|---|---|---|---|
| 1 | OH | H | 2-chlorobenzyl | 2-chlorobenzyl-4-hydroxyproline-benzimidazole amide | 385 (M + H$^+$) |
| 2 | OH | H | 2,6-dichlorobenzyl | 2,6-dichlorobenzyl-4-hydroxyproline-benzimidazole amide | 419 (M + H$^+$) |

TABLE 1a-continued
4-hydroxyproline derivatives containing unsubstituted benzimidazole
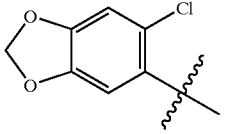
Y = H  R2 = 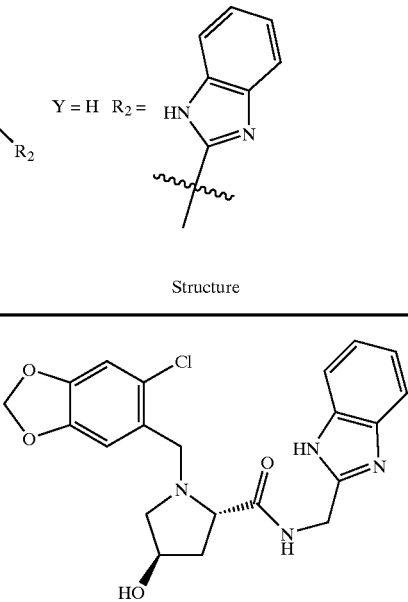
| Cmpd. | X | Z | R1 | Structure | MS Data |
|---|---|---|---|---|---|
| 3 | OH | H | 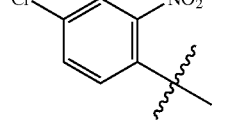 | 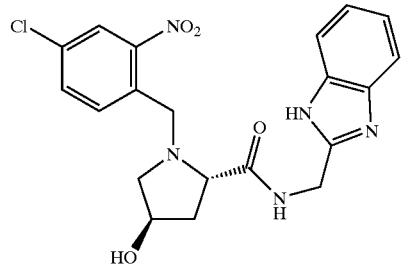 | 429 (M + H⁺) |
| 4 | OH | H | 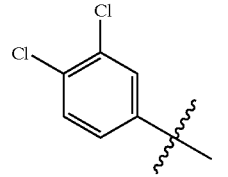 | 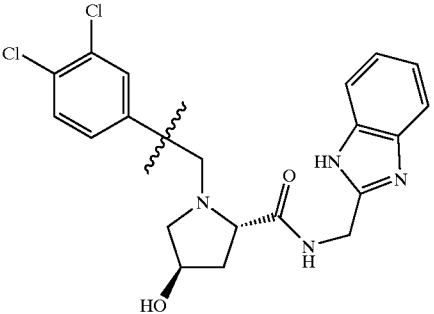 | 430 (M + H⁺) |
| 5 | OH | H | 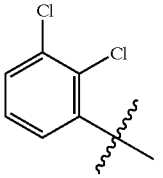 | 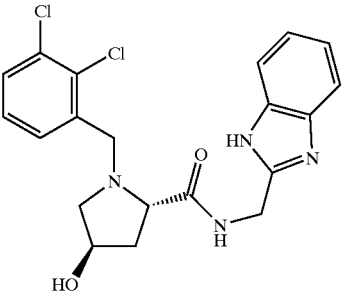 | 419 (M + H⁺) |
| 6 | OH | H |  | 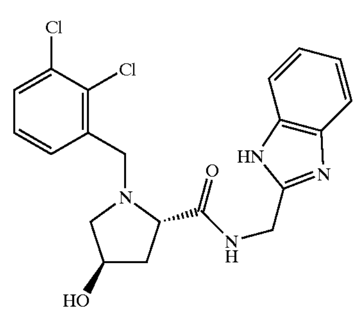 | 419 (M + H⁺) |

TABLE 1a-continued 4-hydroxyproline derivatives containing unsubstituted benzimidazole

Y = H  R2 =

| Cmpd. | X | Z | R1 | Structure | MS Data |
|---|---|---|---|---|---|
| 7 | OH | H | 2,5-dichlorobenzyl | 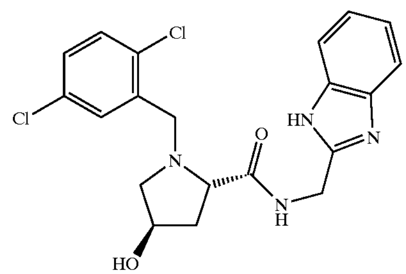 | 419 (M + H⁺) |
| 8 | OH | H | 2,4-dichlorobenzyl | 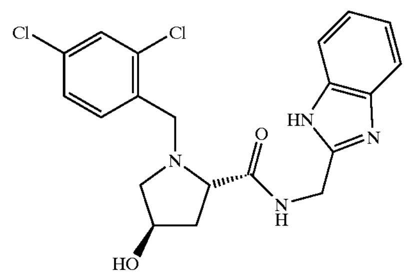 | 419 (M + H⁺) |
| 9 | OH | H | [2-(4-chlorophenyl)thiazol-4-yl]methyl | 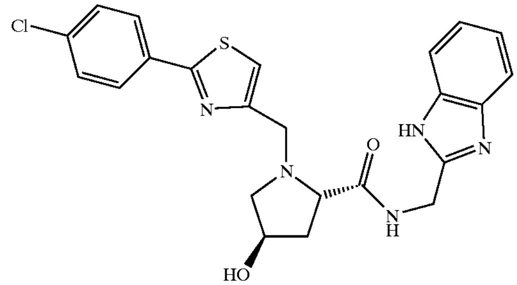 | 468 (M + H⁺) |
| 10 | H | OH | 2,4-dichlorobenzyl | 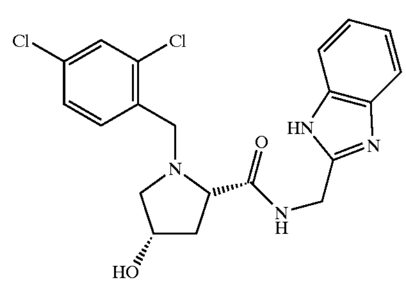 | 419 (M + H⁺) |

TABLE 1a-continued 4-hydroxyproline derivatives containing unsubstituted benzimidazole

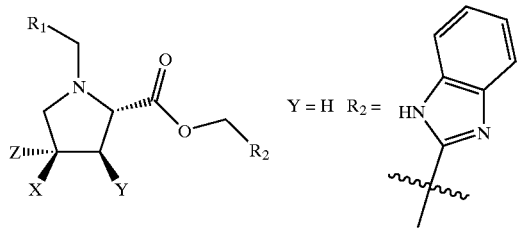

Y = H  R₂ =

| Cmpd. | X | Z | R1 | Structure | MS Data |
|---|---|---|---|---|---|
| 11 | H | H | 2,4-dichlorobenzyl | (structure shown) | 403 (M + H⁺) |

TABLE 1b trans-4-hydroxyproline derivatives containing substituted benzimidazoles

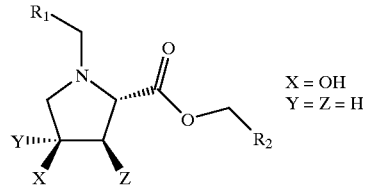

X = OH
Y = Z = H

| Cmpd | R1 | R2 | Structure | MS Data |
|---|---|---|---|---|
| 12 | 2,4-dichlorophenyl | 4,5-dimethylbenzimidazol-2-yl | (structure shown) | 447 (M + H⁺) |
| 13 | 2,4-dichlorophenyl | 5-(methoxycarbonyl)benzimidazol-2-yl | (structure shown) | 477 (M + H⁺) |

TABLE 1b-continued trans-4-hydroxyproline derivatives containing
substituted benzimidazoles

X = OH
Y = Z = H

| Cmpd | R1 | R2 | Structure | MS Data |
|---|---|---|---|---|
| 14 | 2,4-dichlorophenyl | 5-chloro-1H-benzimidazol-2-yl | 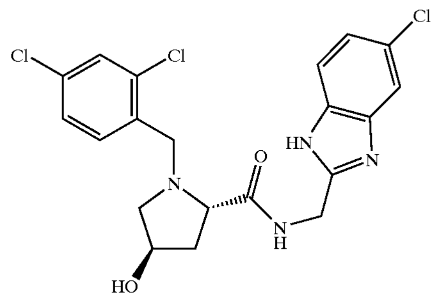 | 453 (M + H$^+$) |
| 15 | 2,4-dichlorophenyl | 5,6-dichloro-1H-benzimidazol-2-yl | 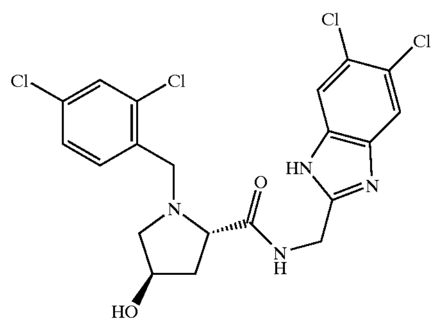 | 487 (M + H$^+$) |

TABLE 2a trans-3-hydroxyproline derivatives
containing unsubstituted benzimidazoles X = Y = H   R$_2$ = 1H-benzimidazol-2-yl
Z = OH

| Cmpd | R1 | Structure | MS Data |
|---|---|---|---|
| 16 | 2,4-dichlorophenyl | 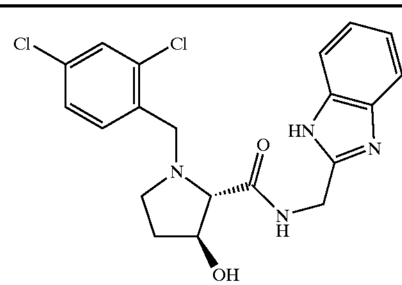 | 419 (M + H$^+$) |

TABLE 2a-continued
trans-3-hydroxyproline derivatives
containing unsubstituted benzimidazoles
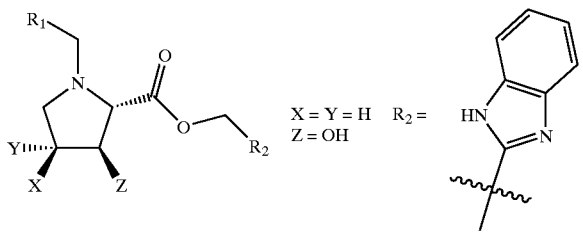
X = Y = H  R₂ = (benzimidazol-2-ylmethyl)
Z = OH
| Cmpd | R1 | Structure | MS Data |
|------|----|-----------|---------|
| 17 | 6-chloro-1,3-benzodioxol-5-yl | 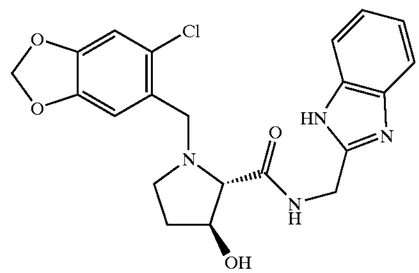 | 429 (M + H⁺) |
| 18 | 2-(4-chlorophenyl)thiazol-4-yl | 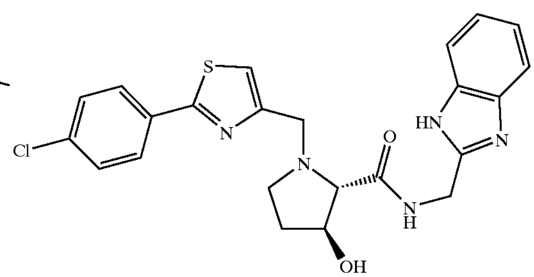 | 468 (M + H⁺) |
| 19 | 2,6-dichlorophenyl | 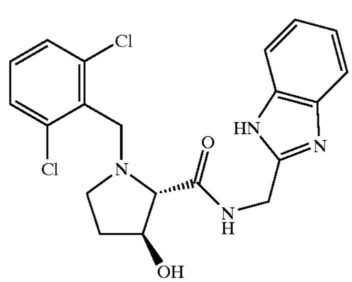 | 419 (M + H⁺) |

TABLE 2b trans-3-hydroxyproline derivatives containing substituted benzimidazoles

X = Y = H
Z = OH

| Cmpd | R1 | R2 | Structure | MS Data |
|---|---|---|---|---|
| 20 | 2,6-dichlorophenyl-CH< | 4,5-dimethylbenzimidazol-2-yl-CH< | 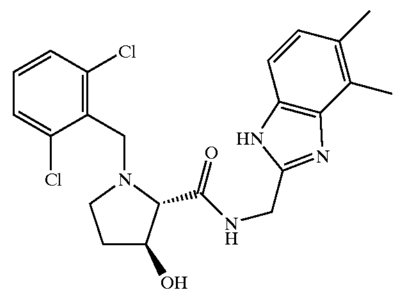 | 447 (M + H⁺) |
| 21 | 2,6-dichlorophenyl-CH< | 5-(methoxycarbonyl)benzimidazol-2-yl-CH< | 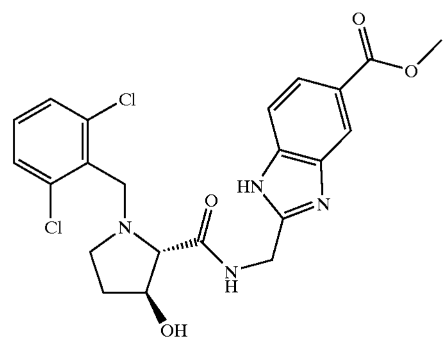 | 477 (M + H⁺) |
| 22 | 2,6-dichlorophenyl-CH< | 5-chlorobenzimidazol-2-yl-CH< | 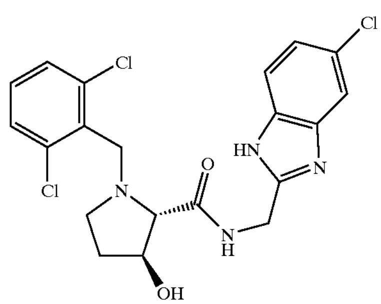 | 453 (M + H⁺) |
| 23 | 2,4-dichlorophenyl-CH< | 5-chlorobenzimidazol-2-yl-CH< | 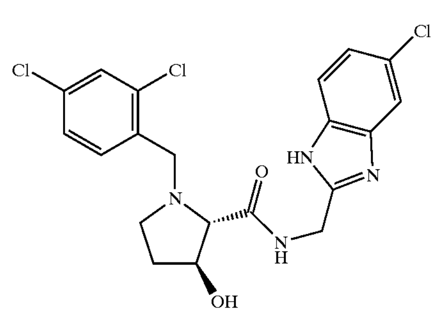 | 453 (M + H⁺) |

TABLE 2b-continued trans-3-hydroxyproline derivatives
containing substituted benzimidazoles

X = Y = H
Z = OH

| Cmpd | R1 | R2 | Structure | MS Data |
|---|---|---|---|---|
| 24 | 2,4-dichlorobenzyl | 5,6-dichloro-1H-benzimidazol-2-yl | 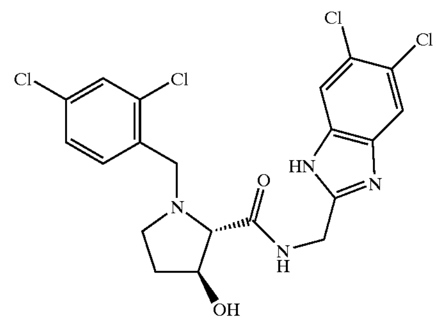 | 487 (M + H$^+$) |
| 25 | 2-(4-chlorophenyl)thiazol-4-yl | 4,5-dimethyl-1H-benzimidazol-2-yl | 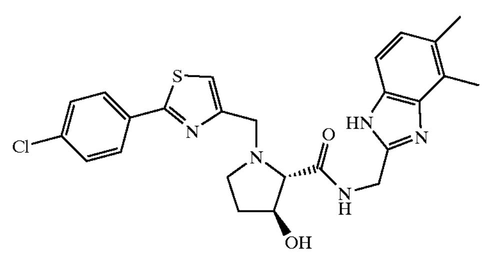 | 496 (M + H$^+$) |
| 26 | 2-(4-chlorophenyl)thiazol-4-yl | 5-(methoxycarbonyl)-1H-benzimidazol-2-yl | 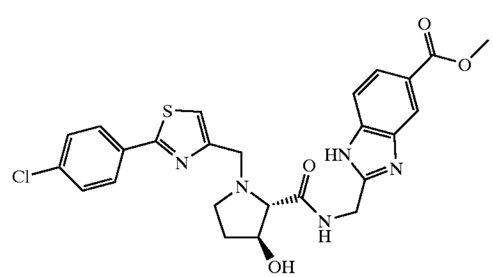 | 426 (M + H$^+$) |
| 27 | 2-(4-chlorophenyl)thiazol-4-yl | 5-chloro-1H-benzimidazol-2-yl | 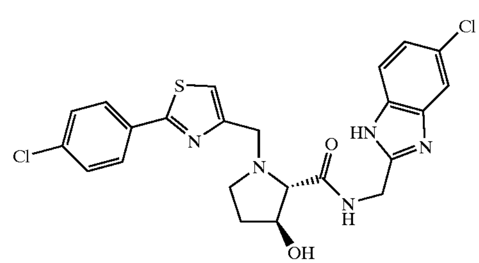 | 502 (M + H$^+$) |

TABLE 2b-continued
trans-3-hydroxyproline derivatives
containing substituted benzimidazoles
X = Y = H
Z = OH
| Cmpd | R1 | R2 | Structure | MS Data |
|------|----|----|-----------|---------|
| 28 | | | 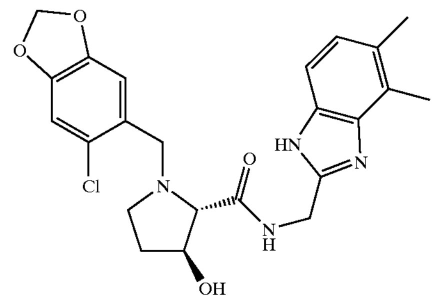 | 457 (M + H⁺) |
| 29 | | | 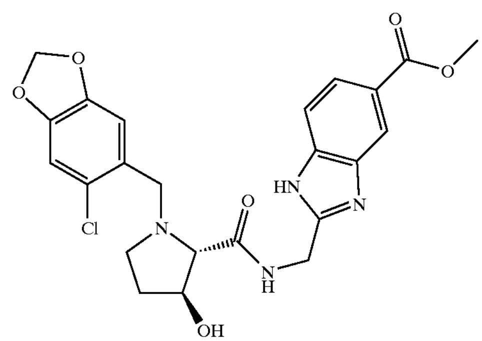 | 487 (M + H⁺) |
| 30 | | | 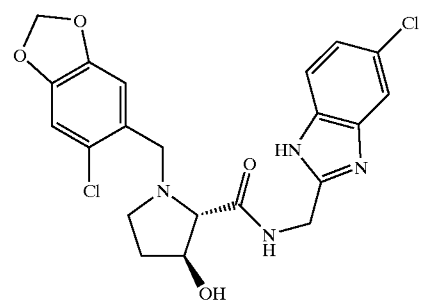 | 463 (M + H⁺) |
Scheme IV
Synthesis X
Modular Synthesis of 4-Hydroxyproline
Analogues using Reductive Amination
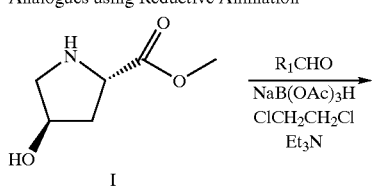
-continued
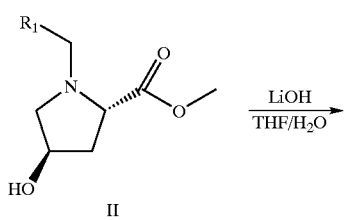

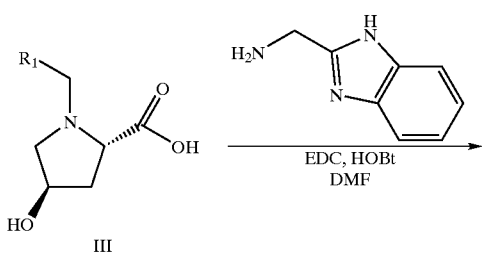

To a solution of trans-4-hydroxy-L-proline methyl ester hydrochloride (I, 2.07 mmol, 300 mg) and aldehyde (R₁CHO, 2.07 mmol) in 7 ml of dichloethylene were added triethylamine (4.14 mmol, 0.58 ml) and sodiumtriacetoxyborohydride (2.9 mmol, 613 mg). The cloudy reaction mixture was stirred at room temperature for 3 hr then quenched with saturated aqueous sodium bicarbonate (6 ml). The aqueous layer was extracted three times with 7 ml of ethyl acetate. The organic layers were combined, dried over anhydrous sodium sulfate and stripped in vacuo to yield a product requiring no further purification, as judged by its LC/MS trace.

The alkylated proline methyl ester (II) was elaborated to final amide (IV) using the procedure described in Scheme III.

Table 3, below, provides examples of alkylated prolines obtained through reductive amination.

TABLE 3 trans-4-hydroxyproline derivatives synthesized using reductive amination

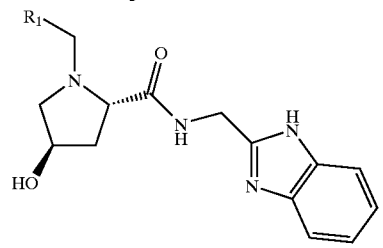

| Cmpd. | R1 | Structure | MS Data |
|---|---|---|---|
| 31 | (4-Br-phenyl)-CH₂- | (structure) | 429 (M + H⁺) |
| 32 | (pentafluorophenyl)-CH₂- | (structure) | 441 (M + H⁺) |

TABLE 3-continued trans-4-hydroxyproline derivatives synthesized using reductive amination

| Cmpd. | R1 | Structure | MS Data |
|---|---|---|---|
| 33 | 4-Br, 2-F phenyl | (structure shown) | 447 (M + H+) |
| 34 | 3,5-dichloro-2-hydroxyphenyl | (structure shown) | 435 (M + H+) |
| 35 | 5-Br, 2-ethoxyphenyl | (structure shown) | 473 (M + H+) |
| 36 | 2,3,5-trichlorophenyl | (structure shown) | 453 (M + H+) |

TABLE 3-continued
trans-4-hydroxyproline derivatives synthesized using reductive amination
| Cmpd. | R1 | Structure | MS Data |
|---|---|---|---|
| 37 | 4-(F$_3$C)-C$_6$H$_4$-CH- | 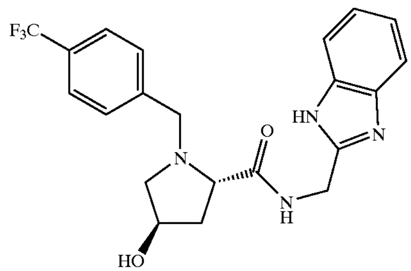 | 419 (M + H$^+$) |
| 38 | 4-Br-thiophen-2-yl-CH- | 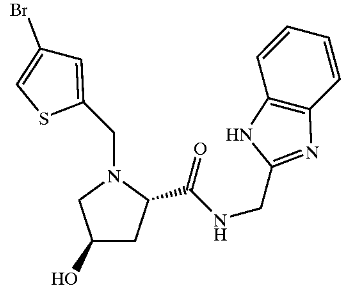 | 435 (M + H$^+$) |
| 39 | 4-Cl-C$_6$H$_4$-CH- | 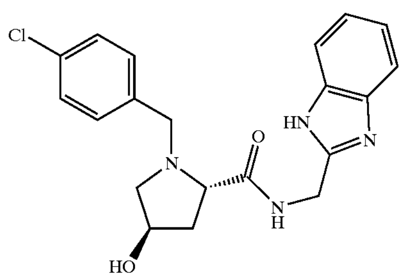 | 485 (M + H$^+$) |
Scheme V
Synthesis XI
Alkylation of Trans 3- and 4-Hydroxyproline
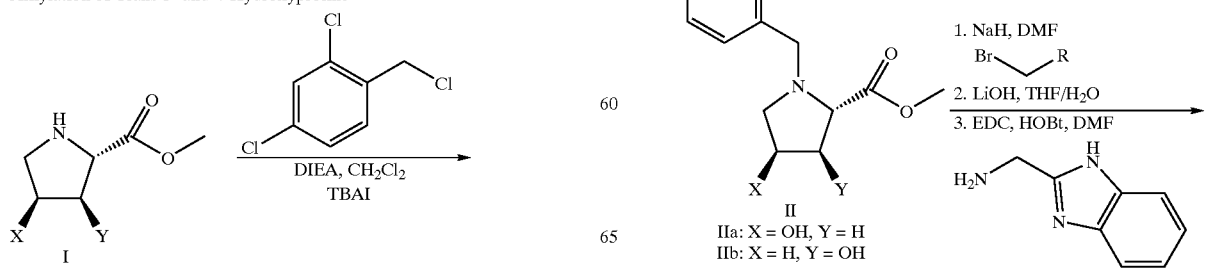
IIa: X = OH, Y = H
IIb: X = H, Y = OH
-continued

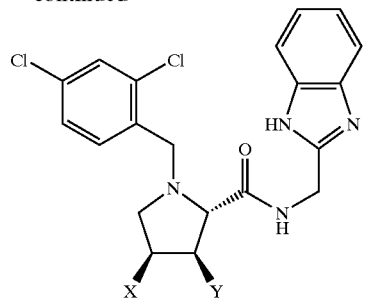

IIIa: X = OCH₂R, Y = H
IIIb: X = H, Y = OCH₂R

To a solution of methyl ester (II, 0.1 mmol, 30 mg) in 1 ml of anhydrous DMF were added sequentially sodium hydride (60mol %, 0.11 mmol, 3 mg) and alkyl bromide. The reaction was stirred at room temperature for 16 hr. Crude reaction mixture was analyzed by LC/MS and showed alkylated product as the major UV component of the trace. The reaction was quenched with 2 ml of 1:1 THF/H$_2$O mixture, then lithium hydroxide monohydrate was added (0.2 mmol, 5 mg) to the reaction. After 2 hr, reaction mixture was worked up as described in Scheme III (hydrolysis of methyl esters). The final amide products were prepared as described in Scheme III.

Compounds 44 and 47 of Table 4 were prepared by cleavage of the corresponding tert-butyl esters, compounds 43 and 46, respectively. The cleavage was carried out in 1 ml of 40% trifluoroacetic acid in dichloromethane over 1 hr. The final products were isolated by evaporation of solvent in vacuo and characterized by LC/MS.

Table 4, below, provides examples of 3- and 4-alkoxyproline derivatives.

TABLE 4

3- and 4-alkoxyproline derivative

| Cmpd. | X | Y | Structure | MS Data |
|---|---|---|---|---|
| 40 | H | ⸻O—CH₂—C≡CH | (2,4-dichlorobenzyl pyrrolidine-2-carboxamide with benzimidazol-2-ylmethyl and 3-propargyloxy) | 457 (M + H⁺) |
| 41 | H | ⸻O—CH₂—C₆H₅ | (2,4-dichlorobenzyl pyrrolidine-2-carboxamide with benzimidazol-2-ylmethyl and 3-benzyloxy) | 509 (M + H⁺) |

TABLE 4-continued 3- and 4-alkoxyproline derivative

| Cmpd. | X | Y | Structure | MS Data |
|---|---|---|---|---|
| 42 | H | —O-allyl | 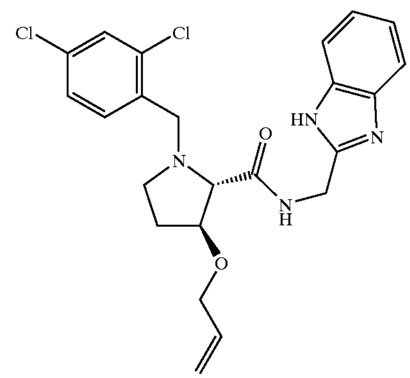 | 459 (M + H$^+$) |
| 43 | H | —O-CH$_2$-C(O)-O-tBu | 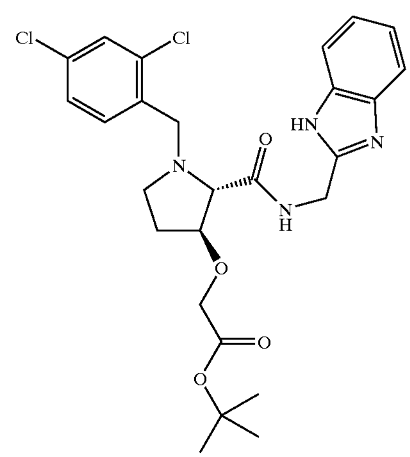 | 533 (M + H$^+$) |
| 44 | H | —O-CH$_2$-C(O)-OH | 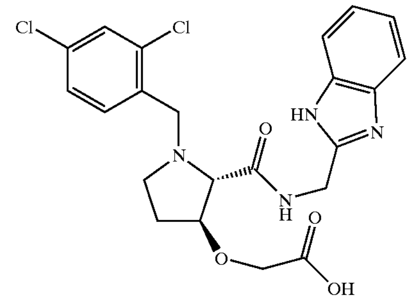 | 477 (M + H$^+$) |

TABLE 4-continued 3- and 4-alkoxyproline derivative

| Cmpd. | X | Y | Structure | MS Data |
|---|---|---|---|---|
| 45 | ⟨O-CH₂-C≡CH⟩ | H | 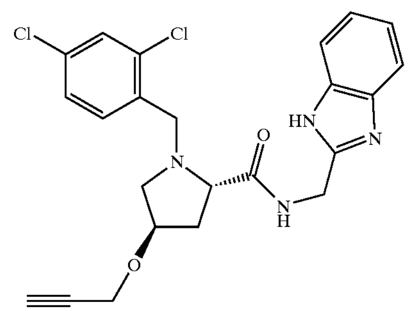 | 457 (M + H⁺) |
| 46 | ⟨O-CH₂-C(O)-O-tBu⟩ | H | 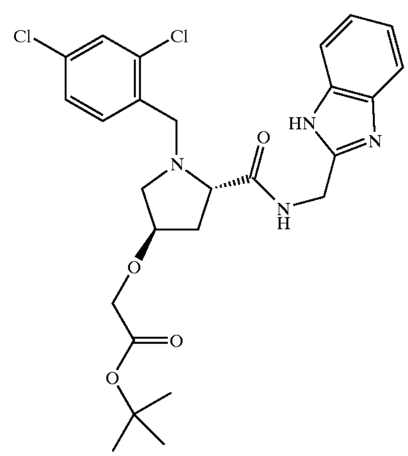 | 533 (M + H⁺) |
| 47 | ⟨O-CH₂-C(O)-OH⟩ | H | 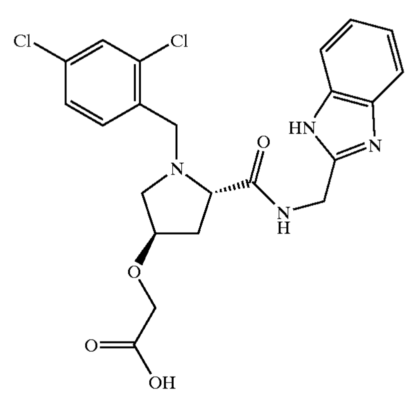 | 477 (M + H⁺) |

TABLE 4-continued 3- and 4-alkoxyproline derivative

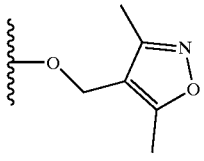

| Cmpd. | X | Y | Structure | MS Data |
|---|---|---|---|---|
| 48 | 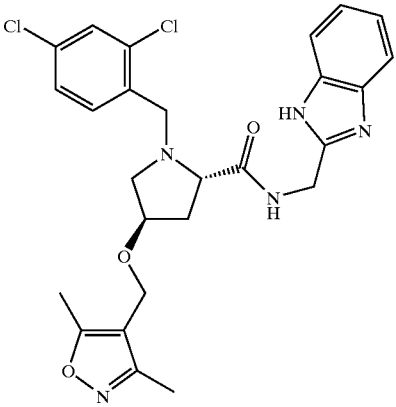 | H | 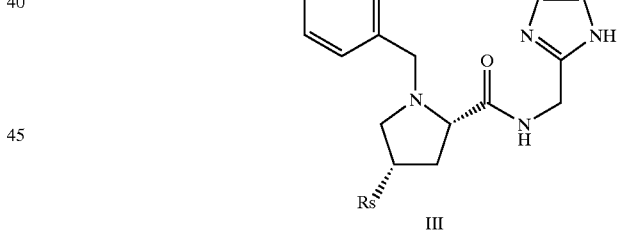 | 528 (M + H+) |

Scheme VI

Synthesis XII
4-Trans-Thioetherproline Analogues

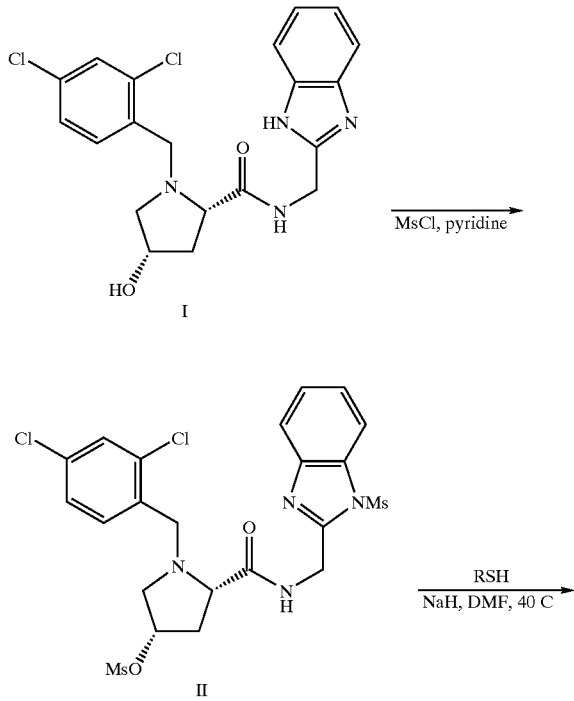

Proline analogue I (Compound 10, Table 1a, 0.17 mmol, 72 mg) was dissolved in 3 ml of dichloromethane and cooled to 0° C. The reaction mixture was treated with anhydrous pyridine (0.7 mmol, 0.06 ml) and methanesulfonyl chloride (0.38 mmol, 0.03 ml). Reaction mixture was slowly warmed up to room temperature over 10 hr then quenched with 5 ml of aqueous saturated sodium bicarbonate. The layers were separated and the aqueous layer washed two more times with 5 ml dichloromethane. The organic layers were combined, dried over anhydrous sodium sulfate and stripped to yield 80 mg of yellowish solid (II) which was characterized by LC/MS (575 M+H+) and required no further purification.

To bismesylate II (20 mg, 0.035 mmol), dissolved in 0.5 ml anhydrous dimethylformamide was added solid sodium hydride (60%, 0.18 mmol, 7 mg). Reaction mixture was placed under nitrogen atmosphere, thiol (0.18 mmol) was added and mixture was heated at 40° C. for 16 h. Reaction was quenched with 2 ml water and washed two times with 3 ml dichloromethane. Organic layers were combined, dried over anhydrous sodium sulfate and evaporated to dryness under stream of nitrogen. Crude products were purified by preparative HPLC as described in Scheme III and isolated as bis TFA salts upon lyophilization.

Compound 49 (Table 5): $\delta_H$(CDCl$_3$): 1.30 (5H, m), 1.62 (1H, m), 1.75 (2H, m), 1.93 (2H, m), 2.58 (2H, m), 2.75 (1H, m), 2.92 (1H, m), 3.60 (1H, m), 3.95 (1H, m), 4.35 (2H, m), 4.54 (1H, m) 5.04 (2H, m), 7.16 (1H, dd, J=8.3 Hz, J=2.0 Hz), 7.48 (2H, m), 7.54 (1H, d, J=8.3 Hz), 7.71 (2H, m).

Compounds 52 and 53 (acids) were prepared by hydrolysis of the corresponding Compounds 51 and 54 (esters), respectively, as described in Scheme III (hydrolysis of methyl esters to acids). The acids were isolated by preparative HPLC followed by lyophilization.

Table 5, below, provides examples of 4-thioether proline derivatives.

TABLE 5

4-thioether proline derivatives

| Cmpd. | R$_1$ | Structure | MS Data |
|---|---|---|---|
| 49 | cyclohexyl | 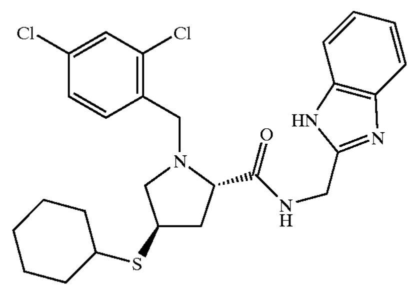 | 517 (M + H$^+$) |
| 50 | —CH$_2$CH$_2$OH | 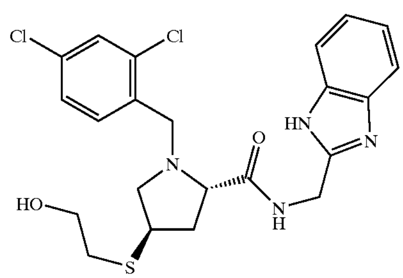 | 479 (M + H$^+$) |
| 51 | —CH$_2$CH$_2$C(O)OCH$_3$ | 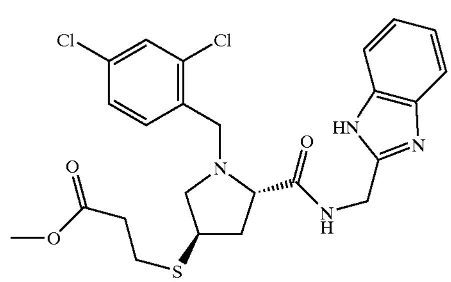 | 521 (M + H$^+$) |

TABLE 5-continued
4-thioether proline derivatives
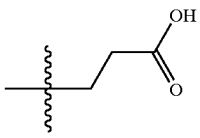
| Cmpd. | R₁ | Structure | MS Data |
|---|---|---|---|
| 52 | 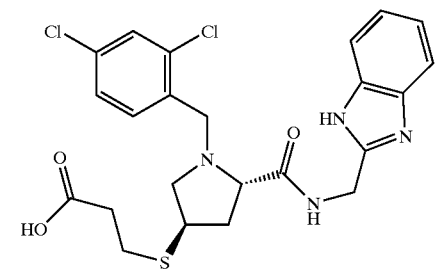 | 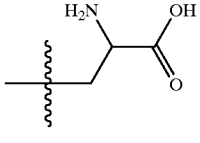 | 507 (M + H⁺) |
| 53 | 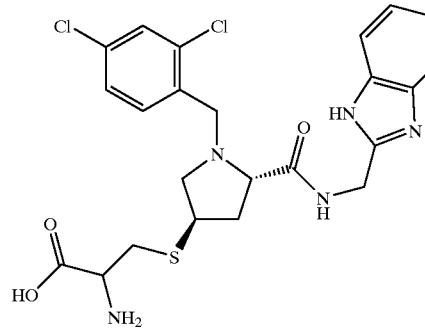 | 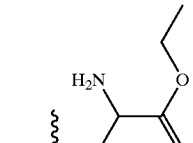 | 522 (M + H⁺) |
| 54 | 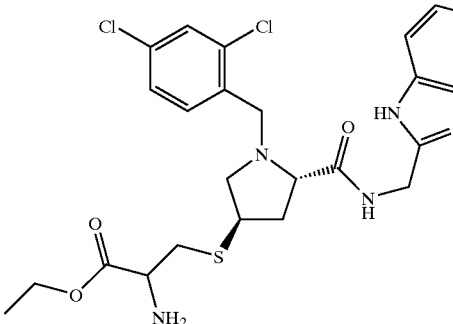 | 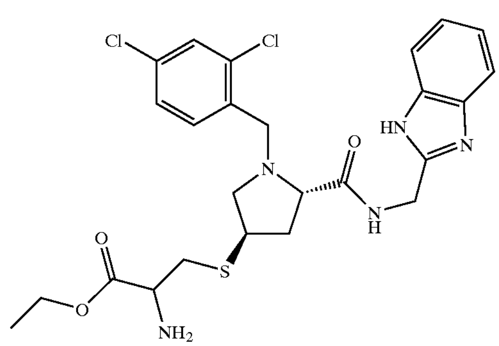 | 550 (M + H⁺) |

Scheme VII

Synthesis XIII
Imidazopyridine and Imidazopyrimidine Derivatives of Proline

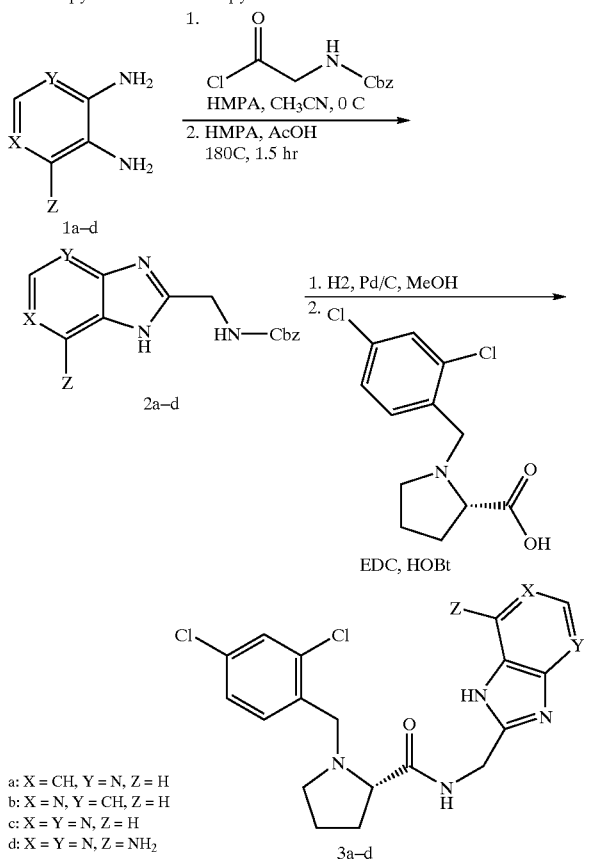

a: X = CH, Y = N, Z = H
b: X = N, Y = CH, Z = H
c: X = Y = N, Z = H
d: X = Y = N, Z = NH$_2$

2-Aminomethylimidazopyridine (2a, b) and 2-aminomethylimidazopyrimidines (2c, d) were prepared by modification of procedure reported by S. Takada et al. (*J. Med. Chem.* 1996, 39, 2844–2851). Sample procedure below describes preparation of 3b. The same method was carried out in preparation of 3a, 3c, and 3d.

A solution of N-Cbz-Glycine (1.5 mmol, 316 mg) in 3 ml of 10:1 mixture of hexamethylphosphoramide (HMPA) and acetonitrile was placed under nitrogen atmosphere and cooled to 0° C. Thionyl chloride was added drop-wise with a syringe over 3 minutes and the solution was stirred at 0° C. After 1 hr, 3,4-diaminopyridine (1b) was added (1.37 mmol, 150 mg). The solution was left in an ice bath for 4 hr, then poured into 50 ml ice-water and neutralized with saturated aqueous sodium bicarbonate. Aqueous layer was washed 4 times with 60 ml of ethyl acetate. The organic washes were combined, dried over anhydrous sodium sulfate and stripped to yield 2.5 ml of yellowish liquid MS (ESI): M+H$^{30}$=301.

The solution was diluted with 3 ml HMPA and 2 ml glacial acetic acid and heated to 180° C. After 1.5 hr, the brown reaction mixture was cooled to room temperature and poured into 70 ml saturated aqueous sodium bicarbonate solution. The aqueous layer was washed 4 times with 100 ml portions of ethyl acetate. The organic washes were combined, dried over anhydrous sodium sulfate and stripped to yield a brown liquid that was divided into 3 portions and each portion dissolved in 2 ml methylene chloride. Each solution was then loaded onto a 2 g strong cation exchange cartridge (Varian Mega Bond Elut SCX) and washed with 5 ml methylene chloride, 10 ml methanol, and finally with 5 ml 2M ammonia/methanol which was collected into a 25 ml round-bottomed flask. The solvent was removed in vacuo to yield 310 mg of 2b; $\delta_H$ (CDCl$_3$): 4.45 (2H, br. s), 4.98 (2H, s), 7.20 (5H, m) 7.45 (1H, d, J=6 Hz), 8.18 (1H, d, J=6 Hz), 8.71 (1H, br. s); MS (ESI) M+H$^+$ 283.

To a solution of 2b (70 mg, 0.25 mmol) in 8 ml of methanol was added 70 mg of 10% Pd/C Degussa type (50% water content). The solution was placed under hydrogen atmosphere and left to stir vigorously at room temperature. After 24 hr, the catalyst was filtered and washed with 50 ml methanol and 3 ml DMF. The filtrates were collected and stripped to yield 35 mg of oily product. The amide 3b was prepared following the amide preparation procedure described for Scheme III.

Table 6, below, provides imidazopyridine and imidazopyrimidine derivatives of proline.

TABLE 6

Imidazopyridine and Imidazopyrimidine Derivatives of Proline

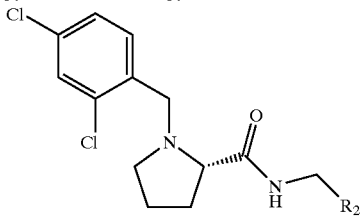

| Cmpd. | R$_2$ | Structure | MS Data |
|---|---|---|---|
| 55 | | 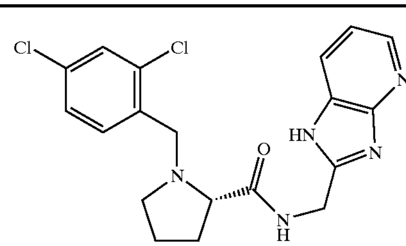 | 404 (M + H$^+$) |

TABLE 6-continued

Imidazopyridine and Imidazopyrimidine Derivatives of Proline

| Cmpd. | R$_2$ | Structure | MS Data |
|---|---|---|---|
| 56 | (4-azaindole-imidazole fragment) | 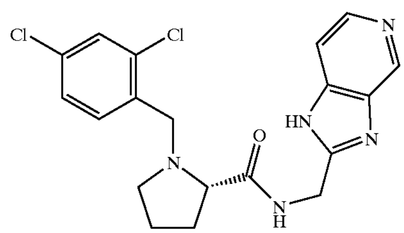 | 404 (M + H$^+$) |
| 57 | (purine fragment) | 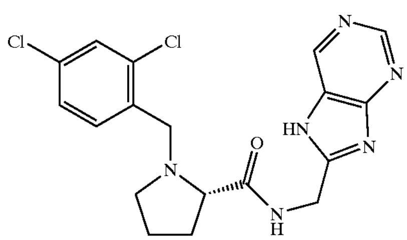 | 405 (M + H$^+$) |
| 58 | (6-amino purine fragment) | 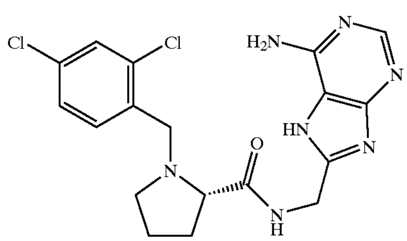 | 420 (M + H$^+$) |

Biological Evaluation

Enzymatic Activity

IC$_{50}$ determinations for the aminoacyl-tRNA synthetases (aaRS) isolated from pathogen or HeLa cells were carried out using a modification of the aaRS charging and trichloroacetic acid precipitation assay described previously (see examples: D. Kern et. al., Biochemie, 61, 1257–1272 (1979) and J. Gilbart et. al. Antimicrobial Agents and Chemotherapy, 37(1), 32–38 (1993)). The aaRS enzymes were prepared via standard cloning and expression methods and partially purified or partially purified from pathogen and HeLa cell extracts. The activity of each aaRS enzyme was standardized as trichloroacetic acid precipitable counts (cpm) obtained at 10 minutes reaction time at Km concentrations of substrates. For practical purposes, the minimal acceptable value is approximately 2000 cpm per 10 minute reaction.

Preincubations for IC$_{50}$ determinations were initiated by incubating partially purified aaRS extracts in 50 mM HEPES (pH 7.5), 0.1 mM EDTA, 0.05 mg/ml bovine serum albumin, 10 mM dithiothreitol and 2.5% dimethyl sulfoxide with and without test compound (e.g. compound of the invention (preferably a compound of Formula I)) in a final volume of 20 microliters in a microtiter plate for 20 minutes at 25° C. Test compounds were typically present as serial dilutions in concentration ranges of 0.35 nM to 35 µM. Test compound solutions were prepared by dissolving test compound in 100% dimethyl sulfoxide and diluting to the final concentration with 50 mM HEPES, pH 7.5. IC$_{50}$ determinations were typically performed in duplicate with each experiment containing 4–8 concentrations of inhibitor along with two no inhibitor controls.

IC$_{50}$ incubations were initiated by supplementing the preincubation mixture to a final assay concentration of 10 mM MgCl$_2$, 30 mM KCl, 10 mM KF, 50 mM HEPES (pH 7.5), 20 µM-500 mM ATP, 2–20 µM [$^3$H] amino acid, and 90–180 µM crude tRNA in a final volume of 35 microliters. The reaction was incubated at 25° C. for 5–20 minutes. At specified time points a 15 microliter aliquot was removed and added to a well of a Millipore filtration plate (Multiscreen-FB, MAFB NOB 10) containing 100 microliters of cold 5% (wt/vol) trichloroacetic acid. Trichloroacetic acid precipitable material was collected by filtration on Millipore Multiscreen filtration station, washed twice with cold 5% trichloroacetic acid, twice with water, and dried. Plates were typically allowed to air dry for several hours or they were baked at 50° C. in a vacuum oven for 30 minutes. The radioactivity on the dried plates was quantitated by the addition of Packard Microscint-20 to the wells and counting with a Packard TopCount scintillation counter.

reader. The MIC value is defined as the lowest compound concentration inhibiting growth of the test organism.

The MIC values (in $\mu$g/ml) of representative compounds of the present invention are listed in Table 8.

TABLE 8

Biological Activity

[Chemical structure shown: 2,4-dichlorobenzyl pyrrolidine with benzimidazole and R5 substituent, linker L]

| CB # | L | R$_5$ | n | MS calcd | MS obsv | +/− ion | IC50 (nM)* Sa | (nM)* Ef | MIC ($\mu$g/mL) Sa | Efs | Efm |
|---|---|---|---|---|---|---|---|---|---|---|---|
| 126,881 | (S)—CONHCH$_2$ | H | 1 | 403.1092 | 403.1109 | + | <500 | <10000 | 100 | <100 | |
| 127,006 | (S)—CONHCH$_2$ | (R, S) OH | 1 | 419.1041 | 419.1030 | + | <500 | <10000 | <100 | <100 | <100 |
| 127,566 | (S)—CONHCH$_2$ | (R, S)-CN | 1 | 428 | 428 | + | <10000 | <10000 | >100 | >100 | >100 |
| 127,889 | (S)—CONHCH$_2$ | (R, S)-OCH$_2$Ph | 1 | 509.1511 | 509.1532 | + | <10000 | <10000 | >100 | >100 | >100 |
| 130,692 | (S)—CONHCH$_2$ | =O | 1 | 417.0885 | 417.0867 | + | <10000 | <10000 | >100 | >100 | >100 |
| 130,693 | (S)—CONHCH$_2$ | H | 2 | 417.1249 | 417.1232 | + | <10000 | <10000 | <100 | >100 | 100 |
| 130,705 | (S)—CONHCH$_2$ | =NNH$_2$ | 1 | 421.1154 | 421.1151 | + | <10000 | <10000 | >100 | >100 | >100 |
| 130,706 | (S)—CONHCH$_2$ | (R, S)-tetrazole | 1 | 471.1215 | 471.1228 | + | <500 | <500 | >100 | >100 | >100 |
| 130,707 | (S)—CONHCH$_2$ | =NOH | 1 | 432.0994 | 432.0985 | + | <10000 | <10000 | >100 | >100 | >100 |
| 130,708 | (S)—CONHCH$_2$ | =NOCH3 | 1 | 446.1150 | 446.1170 | + | <10000 | <10000 | >100 | >100 | >100 |
| 130,709 | (S)—CONHCH$_2$ | =NOCH$_2$CO$_2$H | 1 | 490.1049 | 490.1027 | + | <10000 | <10000 | >100 | >100 | >100 |
| 130,724 | (R)—CONHCH$_2$ | H | 1 | 403.1092 | 403.1104 | + | <10000 | <10000 | <100 | >100 | >100 |
| 130,725 | (R)—CONHCH$_2$ | (R)-OH | 1 | 419.1041 | 419.1029 | + | <60000 | <60000 | >100 | >100 | >100 |
| 130,900 | (S)—CONHCH$_2$ | (S)—OH | 1 | 419.1041 | 419.1061 | + | <500 | <500 | 100 | <100 | 100 |
| 130,901 | (S)—CONHCH$_2$ | (R)-OH | 1 | 419.1041 | 419.1038 | + | <500 | <1000 | <100 | <100 | <100 |
| 130,928 | (S)—CH$_2$OCH$_2$ | H | 1 | 390.1140 | 390.1138 | + | <10000 | <10000 | 100 | >100 | 100 |
| 130,973 | (S)—CONHCH$_2$ | CH$_2$CO$_2$H | 1 | 461.1147 | 461.1126 | + | <500 | <500 | >100 | >100 | >100 |

*<500 = 500 nM or less; <1000 = 501–1000 nM; <10000 = 1001–10000 nM; <60000 = 10001–60000 nM
Sa = S. aureus
EF = E. faecalis
Efm = E. faecium Inhibitor activity was typically reported as a percentage of the control aaRS activity. The IC$_{50}$ value was determined by plotting per cent activity versus compound concentration in the assay and identifying the concentration at which 50% of the activity was remaining.

The IC$_{50}$ values (in $\mu$M) of representative compounds of the present invention are listed in Table 8.

Whole Cell Antimicrobial Screens

Compounds were tested for antimicrobial activity against a panel of organisms according to standard procedures described by the National Committee for Clinical Laboratory Standards (NCCLS document M7-A3, Vol. 13, No. 25, 1993/NCCLS document M27-P, Vol. 12, No. 25, 1992). Compounds were dissolved in 100% DMSO and were diluted to the final reaction concentration (0.1 $\mu$g/ml–500 $\mu$g/ml) in microbial growth media. In all cases the final concentration of DMSO incubated with cells is less than or equal to 1%. For minimum inhibitory concentration (MIC) calculations, 2-fold dilutions of compounds were added to wells of a microtiter plate containing 1×10$^5$ bacteria or fungal cells in a final volume of 200 lambda of an appropriate media (Mueller-Hinton Broth; Haemophilus Test Media; Mueller-Hinton Broth+5% Sheep Blood; or RPMI 1690). Plates were incubated overnight at an appropriate temperature (30° C.–37° C.) and optical densities (measure of cell growth) were measured using a commercial plate In Vivo Efficacy
Mouse Protection Test The mouse protection test is an industry standard for measuring the efficacy of a test compound in vivo [for examples of this model see J. J. Clement, et al., *Antimicrobial Agents and Chemotherapy*, 38 (5), 1071–1078, (1994)]. As exemplified below, this test is used to show the in vivo efficacy of the compounds of the present invention against bacteria or fungi.

The in vivo antimicrobial activity of a compound of the invention (preferably a compound of Formula I) hereinafter referred to as test compound, is established by infecting male or female mice (5 mice/dose group×5 doses/compound) weighing 20–25 g intraperitoneally with pathogen inoculum. The inoculum is prepared from a sample of pathogen obtained from the ATCC (for example, ATCC 29213, *S. aureus*; ATCC 14154, *S. aureus*; ATCC 8668, *Strep. pyogenes*; ATCC 25922, *E. coli*; ATCC 29212, *E. faecalis*; ATCC 25238, *M. catarrhalis*; and ATCC 90028, *C. albicans*). Each bacterial strain is grown in its appropriate medium at 37° C for 18 hr, most strains yielding between 10$^8$ and 10$^9$ colony forming units (CFU)/ml under these conditions. The overnight culture is serially diluted to an appropriate content and then 0.5 ml of each dilution is added to 4.5 ml of 5% hog gastric mucin to prepare the infecting inoculum. Each mouse is injected with 0.5 ml of the inoculum intraperitoneally (i.p.), five animals per dilution. The 50% lethal dose ($LD_{50}$) and the minimal lethal dose (MLD, the dose causing 100% death of the animals) is calculated on the basis of the number of mice surviving after 7 days. The MLD established for each of the pathogens is used as inoculum dose in the mouse protection tests.

The test compound is dissolved in a sterile vehicle appropriate for its method of delivery (for example, 30% HPB (hydroxypropyl-β-cyclodextrin), pH, 7.4 or 0.05M Tris.HCl). A vehicle group (dose=0) serves as a placebo control for each compound and each pathogen. The dose for the test compound is determined based on the MIC data. A series of dilutions of a test compound is prepared in the vehicle. A group of 5 mice are used for each test compound dose and the vehicle. There are 5–6 doses for each compound. Each animal is used for one experiment only.

Mice are infected i.p. with 0.5 ml of the MLD of pathogen in 5% hog gastric mucin by one researcher and immediately administered compound (s.c., p.o. or i.v. in volumes indicated above) by a second researcher. The 50% protective dose ($PD_{50}$) is calculated from the dose response curve established on the basis of the numbers of mice surviving for 7 days after treatment. In each experiment, a group of positive control with a commercially available antibiotic for example, is also included.

All of the references, patents and patent publications identified or cited herein are incorporated, in their entirety, by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method of treating a subject afflicted by or susceptible to an infection, wherein said subject is selected from the group consisting of a mammal, a plant and a culture, said method comprising administering to the subject a therapeutically-effective amount of the compound of the Formula:

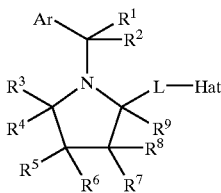

(a) wherein Ar is selected from the group consisting of unsubstituted or substituted aryl, and unsubstituted or substituted heteroaryl;
(b) wherein L is selected from the group consisting of —C(O)N(Q)CH$_2$—, and —CR$^{10}$OR$^{11}$OCR$^{12}$R$^{13}$—; wherein Q is selected from the group consisting of hydrido, —(CH$_2$)$_m$CO$_2$H and —(CH$_2$)$_m$CO$_2$CH$_3$; wherein m is selected from the group consisting of 1, 2, 3, and 4;
(c) wherein each of R$^1$, R$^2$, R$^9$, R$^{10}$, R$^{11}$, R$^{12}$ and R$^{13}$ is independently selected from the group consisting of hydrido and lower alkyl;
(d) wherein each of R$^3$, R$^4$, R$^5$, R$^6$, R$^7$, and R$^8$ is independently selected from the group consisting of hydrido, acyl, amino, cyano, acyloxy, acylamino, carboalkoxy, carboxyamido, carboxy, halo, alkyl, heteroaryl, heterocyclyl, alkoxy, aryloxy, N-sulfonylcarboxyamido, N-acylamino sulfonyl, hydroxy, aryl, and cycloalkyl; alternatively, each of R$^3$ and R$^4$ together, R$^5$ and R$^6$ together, and R$^7$ and R$^8$ together are independently selected from the group consisting of

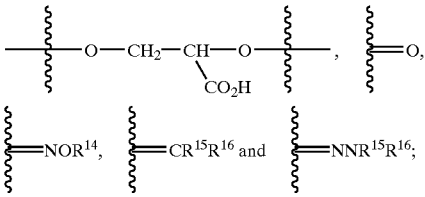

wherein each of R$^{14}$, R$^{15}$ and R$^{16}$ are independently selected from the group consisting of hydrido, alkyl and carboxy substituted alkyl; provided that at least five of R$^3$, R$^4$, R$^5$, R$^6$, R$^7$, and R$^8$ are independently hydrido; alternatively, each of R$^3$, R$^4$, R$^5$, R$^6$, R$^7$, and R$^8$ is independently selected from —O(CH$_2$)$_n$CO$_2$R$^{17}$, —O(CH$_2$)$_n$CONHSO$_2$R$^{18}$, —(CH$_2$)$_n$CO$_2$R$^{19}$, —(CH$_2$)$_n$CONHSO$_2$R$^{20}$, —C(O)NHCH(R$^{22}$)CO$_2$R$^{21}$, or —N(R$^{23}$)(CH$_2$)$_n$CO$_2$R$^{24}$, wherein each of R$^{17}$, R$^{19}$, R$^{21}$, R$^{22}$, R$^{23}$, and R$^{24}$ is independently selected from hydrido or alkyl; wherein each of R$^{18}$ and R$^{20}$ is independently alkyl; wherein n is selected from 1 or 2; and (e) wherein Hat is selected from the group consisting of

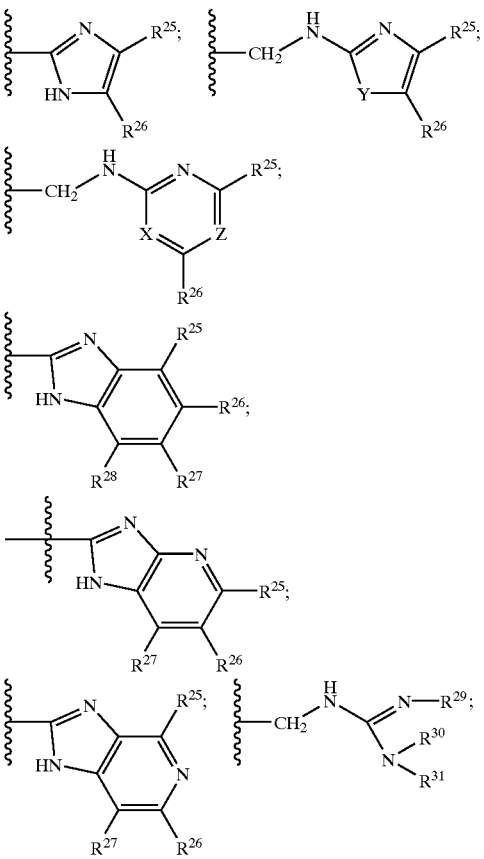

-continued

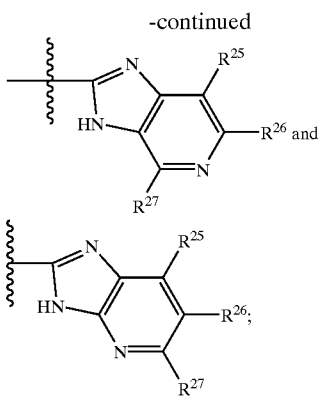

wherein X is selected from the group consisting of N and $CR^{27}$; wherein Y is selected from the group consisting of NH, S and O; wherein Z is selected from the group consisting of N and $CR^{28}$; wherein each of $R^{25}$, $R^{26}$, $R^{27}$, and $R^{28}$ is independently selected from the group consisting of nitro, halo, hydroxy, lower amino, lower alkyl, lower alkoxy, lower carboalkoxy, and carboxy; wherein each of $R^{29}$, $R^{30}$, and $R^{31}$ is selected from the group consisting of hydrido, alkyl, aryl, nitro, and amino;
and pharmaceutically-acceptable salts thereof.

2. The method of claim 1 wherein Ar is aryl and pharmaceutically-acceptable salts thereof.

3. The method of claim 1 wherein L is —C(O)NHCH$_2$— and pharmaceutically-acceptable salts thereof.

4. The method of claim 1 wherein each of $R^1$, $R^2$, $R^9$, $R^{10}$, $R^{11}$, $R^{12}$ and $R^{13}$ is independently hydrido and pharmaceutically-acceptable salts thereof.

5. The method of claim 1 wherein each of $R^3$, $R^4$, $R^5$, $R^6$, $R^7$, and $R^8$ is independently selected from the group consisting of hydrido, hydroxy, alkoxy, alkyl, amino, and carboxyamido; and pharmaceutically-acceptable salts thereof.

6. The method of claim 5 wherein each of $R^3$, $R^4$, $R^5$, $R^6$, $R^7$, and $R^8$ is independently selected from the group consisting of hydrido, —O(CH$_2$)$_n$CO$_2$R$^{17}$, —O(CH$_2$)$_n$CONHSO$_2$R$^{18}$, —(CH$_2$)$_n$CO$_2$R$^{19}$, —(CH$_2$)$_n$CONHSO$_2$R$^{20}$, —C(O)NHCH(R$^{22}$)CO$_2$R$^{21}$, and —N(R$^{23}$)(CH$_2$)$_n$CO$_2$R$^{24}$; wherein each of $R^{17}$, $R^{19}$, $R^{21}$, $R^{22}$, $R^{23}$, and $R^{24}$ is independently selected from hydrido and alkyl; wherein $R^{18}$ and $R^{20}$ are independently alkyl; wherein n is selected from the group consisting of 1 and 2; and pharmaceutically-acceptable salts thereof.

7. The method of claim 6 wherein $R^3$, $R^4$, $R^6$, $R^7$, and $R^8$ are hydrido and $R^5$ is selected from the group consisting of —O(CH$_2$)$_n$CO$_2$R$^{17}$, —O(CH$_2$)$_n$CONHSO$_2$R$^{18}$, —(CH$_2$)$_n$CO$_2$R$^{19}$, —(CH$_2$)$_n$CONHSO$_2$R$^{20}$, —C(O)NHCH(R$^{22}$)CO$_2$R$^{21}$, and —N(R$^{23}$)(CH$_2$)$_n$CO$_2$R$^{24}$ and pharmaceutically-acceptable salts thereof.

8. The method of claim 1 wherein Het is selected from the group consisting of

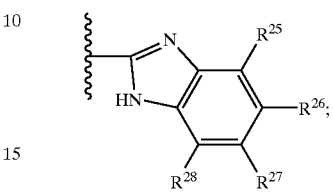

and pharmaceutically-acceptable salts thereof.

9. The method of claim 1 wherein said compound is of the Formula:

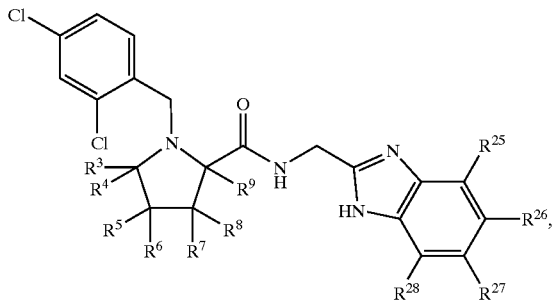

and pharmaceutically-acceptable salts thereof.

10. The method of claim 1 wherein the infection is a bacterial infection.

11. The method of claim 1 wherein the infection is a fungal infection.

12. The method of claim 1 wherein the subject is a mammal.

13. The method of claim 12 wherein the mammal is a human.

* * * * *